United States Patent
Harrington et al.

(10) Patent No.: US 8,089,030 B2
(45) Date of Patent: Jan. 3, 2012

(54) BUCKY WARMER WITH HOLDER

(75) Inventors: Ann Wallin Harrington, Duluth, MN (US); Paul A. Pilosi, Minnetonka, MN (US); Nathanial R. Hallee, Minneapolis, MN (US); Ted Klein, Saint Bonifacius, MN (US)

(73) Assignee: Marvel Concepts, LLC, Duluth, MN (US)

( * ) Notice: Subject to any disclaimer, the term of this patent is extended or adjusted under 35 U.S.C. 154(b) by 464 days.

(21) Appl. No.: 12/272,256

(22) Filed: Nov. 17, 2008

(65) Prior Publication Data
US 2009/0145893 A1 Jun. 11, 2009

Related U.S. Application Data

(63) Continuation-in-part of application No. 11/549,250, filed on Oct. 13, 2006, now abandoned, which is a continuation-in-part of application No. 11/333,922, filed on Jan. 18, 2006, now abandoned.

(60) Provisional application No. 60/644,868, filed on Jan. 18, 2005, provisional application No. 60/739,978, filed on Nov. 25, 2005.

(51) Int. Cl.
  A61B 6/00 (2006.01)
  A61B 6/04 (2006.01)
  H05B 3/20 (2006.01)
  H05B 3/22 (2006.01)
  H05B 3/30 (2006.01)

(52) U.S. Cl. ........ 219/228; 219/245; 219/246; 219/247; 219/535; 378/37; 378/177; 378/208; 378/210

(58) Field of Classification Search .................. None
See application file for complete search history.

(56) References Cited

U.S. PATENT DOCUMENTS

| | | | |
|---|---|---|---|
| 3,035,144 A | | 5/1962 | Kircher |
| 3,168,641 A | * | 2/1965 | Hanusiak .................... 219/250 |
| 3,319,045 A | * | 5/1967 | Tucker ......................... 219/243 |
| 3,356,825 A | | 12/1967 | Mills et al. |
| 4,495,402 A | | 1/1985 | Burdick et al. |
| 4,527,824 A | | 7/1985 | Rosenfeld |
| 4,736,088 A | | 4/1988 | Bart |
| 4,868,898 A | | 9/1989 | Seto |
| 5,028,295 A | * | 7/1991 | Cracchiolo .................. 156/574 |
| 5,077,855 A | | 1/1992 | Ambasz |
| 5,081,657 A | * | 1/1992 | Klawitter et al. ............. 378/37 |
| 5,117,092 A | * | 5/1992 | Shimizu et al. ............. 219/247 |

(Continued)

OTHER PUBLICATIONS

Markle et al. "Reduction of Discomfort During Mammography Utilizing a Radiolucent Cushioning Pad", 2004 Blackwell Publishing Inc., The Brat Journal, vol. 10, No. 4, 2004 pp. 345-349.

(Continued)

*Primary Examiner* — Joseph M Pelham
(74) *Attorney, Agent, or Firm* — Drinker Biddle & Reath LLP

(57) ABSTRACT

A portable device is provided that is used to warm a mammography machine and which comprises a warmer and a holder for the warmer, the holder having a charging mechanism for charging the warmer. The warmer includes an enclosed heating element and power source. The heating element is precisely regulated to ensure that the sensitive imaging elements are not damaged by an over-temperature condition, while at the same time permitting a rapid heating of the warmer for high cycle use. The warmer warms surfaces of the mammography machine that contacts human skin.

23 Claims, 18 Drawing Sheets

U.S. PATENT DOCUMENTS

| | | |
|---|---|---|
| 5,138,138 A | 8/1992 | Theilacker et al. |
| 5,157,318 A | 10/1992 | Wang |
| 5,320,162 A | 6/1994 | Seaman |
| 5,659,656 A * | 8/1997 | Das .................................. 392/386 |
| 5,680,503 A * | 10/1997 | Abe et al. ......................... 392/485 |
| 5,751,074 A * | 5/1998 | Prior et al. ....................... 307/118 |
| 5,864,122 A * | 1/1999 | Brandolini et al. ............ 219/483 |
| 6,124,578 A * | 9/2000 | Elliot ............................. 219/528 |
| 6,172,335 B1 * | 1/2001 | Goodrich ....................... 219/251 |
| 6,190,334 B1 | 2/2001 | Lasky et al. |
| 6,542,705 B2 * | 4/2003 | Fujita et al. ..................... 399/69 |
| 6,723,960 B2 | 4/2004 | DiMartino et al. |
| 6,765,984 B2 | 7/2004 | Higgins et al. |
| 6,850,590 B2 | 2/2005 | Gaikin |
| 6,967,309 B2 * | 11/2005 | Wyatt et al. ..................... 219/217 |
| 6,968,033 B2 | 11/2005 | Lebovic et al. |
| 7,196,289 B2 * | 3/2007 | Ellis et al. ....................... 219/217 |
| 7,251,309 B2 | 7/2007 | Galkin |
| 7,508,905 B2 * | 3/2009 | Bohrisch et al. ................ 378/37 |
| 7,569,796 B2 * | 8/2009 | Kaiser et al. ................... 219/260 |
| 2002/0043523 A1 * | 4/2002 | Fujita et al. .................... 219/216 |
| 2003/0043576 A1 | 3/2003 | Maglica et al. |
| 2003/0153805 A1 | 8/2003 | Gryn et al. |
| 2003/0218003 A1 | 11/2003 | Ellis et al. |
| 2004/0112891 A1 | 6/2004 | Ellis et al. |
| 2006/0186297 A1 | 8/2006 | Lore |
| 2007/0045276 A1 * | 3/2007 | Fisher et al. ................... 219/268 |

OTHER PUBLICATIONS

NIST Report, Recycling Advanced Composites, Dec. 1995, NIST, pp. 4 and Appendix I.

Tuite, "Get the Lowdown on Ultracapacitors," Electronicdesign.com [online]. Penton Media Inc., Nov. 15, 2007 [retrieved on Dec. 28, 2009]. Retrieved from http://electronicdesign.com/content/print.aspx?topic=get-the-lowdown-on-ultracapacitors17465.aspx.

Watlow Electric manufacturing Company Brochure, "Silicone Rubber Heaters," dated 2001.

muRata Brochure, "NTC Thermistors for Temperature Sensor lead Insulation Type".

Maxwell Technologies Brochure, "MC Power Series BOOSTCAP Ultrapacitors".

* cited by examiner

BUCKY WARMER WITH HOLDER

CROSS-REFERENCE TO RELATED APPLICATIONS

The present application is a continuation-in-part of U.S. patent application Ser. No. 11/549,250, filed Oct. 13, 2006, now abandoned which is a continuation-in-part of U.S. patent application Ser. No. 11/333,922, filed Jan. 18, 2006, now abandoned which claims the benefit of U.S. Provisional Patent Application No. 60/644,868, filed Jan. 18, 2005, and U.S. Provisional Patent Application No. 60/739,978, filed Nov. 25, 2005, both herein incorporated by reference.

BACKGROUND

This invention relates to improved comfort and relaxation during medical examination procedures, particularly mammography procedures, by providing relief from related cold stress induced by contact with cold surfaces of medical apparatuses. Patients regularly complain about tension and discomfort resulting from cold X-ray machine surfaces (such as the bucky cover), where, e.g., in a mammogram, these surfaces make contact with exposed breast tissue and surrounding skin. The purpose of this invention is to provide relief from the tension/discomfort that results from cold machine surfaces against exposed skin, such as during mammography.

Having a mammogram is considered by many women and men, to be a stressful and painful experience due to the following factors: a) the ever-present threat of receiving an atypical or breast cancer test result/diagnosis; b) the intense pressure/discomfort/tension described by the majority of patients caused by the required squeezing action of the mammography X-ray machine surfaces compressing the breast tissue; c) the discomfort/tension resulting from cold room temperature machine surfaces (approx. 68-70° F.) contacting their exposed skin (approx. 98° F.), which is a difference of approx. 28-30° F.; and d) the cumulative discomfort/stress experienced by many patients who are required to receive multiple/additional mammogram views needed due to "poor tissue visibility" on initial tests or perhaps needed due to multiple same day mammograms required as part of further diagnostic procedures required to rule out cancer or to prepare for surgical procedures.

A typical mammography machine 100 will have (FIG. 4A) an imaging source and an imaging detector, otherwise referred to as a "grid" (not shown) that lies below a covering called the bucky 110. The bucky 110 is a plate of material that is transparent to the wavelength of the imaging source, such as carbon/graphite. The bucky 110 has a top surface 112 that contacts skin on the bottom of the breasts, and a front surface 114 that contacts skin on the chest. A paddle 110' is used to flatten and compress the breasts so that the imaging system can produce the most beneficial image. The paddle 110' comprises a lower surface 112' that contacts skin on the top of the breasts and a front surface 114' that may or may not contact the patient's skin.

SUMMARY

The goal of this invention is to solve the problem of mammography-related cold-stress. Various embodiments of the invention are considered that can significantly enhance patient comfort and relaxation, thereby allowing more complete mammography tissue compression and thus, better diagnostic images These embodiments can protect sensitive and expensive mammography X-Ray machines from damage due to an over-temperature condition that could damage sensitive bucky mechanisms, rendering the machine inoperable.

These embodiments can also address patient complaints, staff requests for easy to use equipment, safety needs of X-Ray machine manufacturers and budget constraints of clinics/hospitals by creating a device that is: affordable, safe for patient and machine (controlled, monitored temperature for care of X-ray machine), cordless, easy/efficient to use in busy clinics, reusable and thus environmentally responsible, and furthermore can be configured in a simple and pleasing manner.

Accordingly, one embodiment is provided of an apparatus for warming one or more surfaces of a diagnostic or therapeutic instrument, such as a mammography machine: a heater, comprising: an enclosed heating element; a non-insulating filler material adjacent to at least a portion of the heating element; a surface contacting layer of material located on a side of the filler material opposite the heating element; an insulation layer partially surrounding the filler material; and power input terminals that provide external power used to heat the heating element; the heater being designed to transfer heat from the heater to the one or more surfaces of the mammography machine when brought into contact with the one or more surfaces of the mammography machine. The apparatus further comprising a holder, comprising: an affixing mechanism that attaches to an external surface; and a holding mechanism that maintains the heater within the holder when the heater is placed in the holder; the apparatus further comprising a temperature regulator that is either a part of the heater or a part of the holder and regulates the temperature of the heater.

In another embodiment, an apparatus for warming one or more surfaces of a medical diagnostic or therapeutic instrument, comprises a holder and a detachable warmer. The holder comprises: an enclosed heating element; a heat conducting filler material adjacent to at least a portion of the heating element on a heating surface of the holder; power terminals that conduct power used to heat the heating element; and a precision temperature regulator that precisely regulates a temperature of the heater or the heating surface. The detachable warmer comprises: a heat conducting plate; a thin laminate of heat conducting material that on one if its surfaces is affixed the heat conducting plate, and an opposite surface of the thin laminate is designed to be generally entirely in contact with the heating surface of the holder when placed in the holder, and to be generally entirely in contact with the surface of the medical instrument when used to heat the surface of the medical instrument; wherein the contact of the warmer with the holder transfers heat from the holder to the warmer, and the contact of the warmer with the medical instrument transfers heat stored in the warmer to the medical instrument.

In another embodiment of the invention, a portable apparatus is provided for warming one or more surfaces of a medical diagnostic or therapeutic instrument, comprising: a housing comprising a heat plate that forms a lower surface of the housing, the heat plate designed to contact a surface of the medical diagnostic or therapeutic instrument; a handle affixed to the housing; wherein the housing contains within: a heating element; a power supplying element that powers the heating element; a power terminal for providing power to the power supplying element; and a precision temperature regulator that precisely regulates a temperature of the heat plate.

A system is also provided comprising: the portable apparatus for warming, described above; a holder that holds the portable warming apparatus, the holder further comprising: one or more surfaces that generally mate with surfaces of the portable apparatus for holding the portable apparatus in a generally fixed position; and a receiving element to receive the power terminal of the portable apparatus for warming and provide power to the power supplying element.

DESCRIPTION OF THE DRAWINGS

The invention is described below with reference to various preferred embodiments illustrated in the drawings and the following descriptive text.

DETAILED DESCRIPTION OF THE PREFERRED EMBODIMENTS

Figure 1:
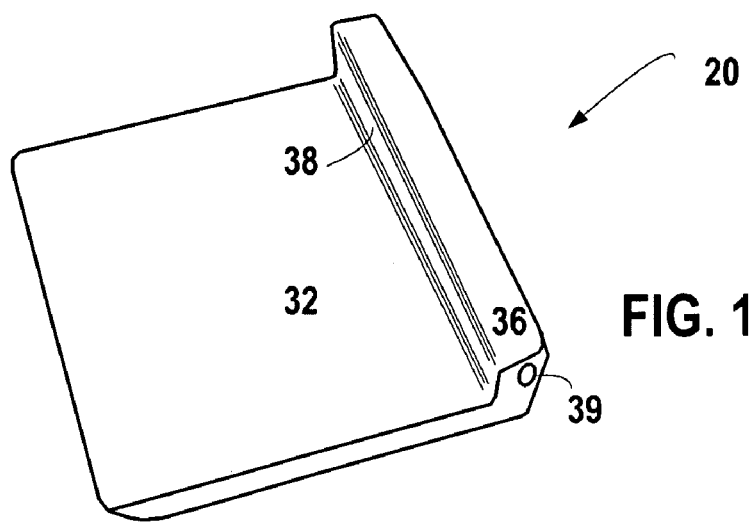
FIG. 1 is a perspective underside view of a bucky warmer showing the surface of the device that contacts the bucky surface during mammography procedures.

FIG. 1 is a perspective underside view of a bucky warmer 20 constructed in accordance with an embodiment of the invention, showing the bottom surface 32 of the device that contacts the bucky top surface 112 (FIG. 4A) during mammography procedures. The this bottom surface 32 that serves as the heating surface of the bucky warmer 20 comprises a relatively thin cover layer 28, such as automotive quality flocked cloth, providing extremely low possibility for abrasion, preventing marking of the fragile carbon composite bucky cover on mammography machines. Any form of covering 28 that serves to separate the interior of the bucky warmer 20 from the bucky top surface 112 is within the scope of the invention, however. The bucky warmer 20 comprises an angled end 36 that gives it an L-shaped cross section. This angled end 36 comprises an inside surface 38 that is used to contact and warm the bucky side surface 114.

The bucky warmer 20 may comprise a user interface portion 44, such as an indicator, display or control panel. For models in which a low cost design is desired, the user interface portion 44 in the form of an indicator such as an LED could be used to show when the unit has attained a desired temperature for use. A user interface portion 44 in the form of a display such as a simple LCD screen to a sophisticated graphical display could be provided to actually display the temperature of the device, the time remaining for heating up to the desired temperature for use, or the time remaining for bringing the bucky surface 112 to temperature, any maintenance or cleaning requirements, number of use cycles, error messages, or any other operational parameters.

In the high cost design models, a user interface portion 44 in the form of a small control panel could be provided with a user interface that would permit an interaction with a processor 40 of the warmer 20. For example, a desired temperature of the warmer 20 or the bucky surface 112 could be assigned by use of a small keypad, control wheels, buttons, joystick, or any other control panel mechanisms that are known in the art. In more sophisticated models, a table of different temperatures (for different machines), power settings and the like for different mammography machine types could be included, and a user could select their appropriate device with the control panel. It is also possible that any indicator, display, or control panel be associated with the holder 50 alternately or additionally.

The warmer 20 is designed to withstand dropping and rough usage with no effect on the unit's operation, and therefore, ideally, comprises a single-piece generally uniform contoured body (i.e., with out any removable pieces in the course of normal operation) as illustrated in the figures, although numerous variants can also be considered.

Figure 2:
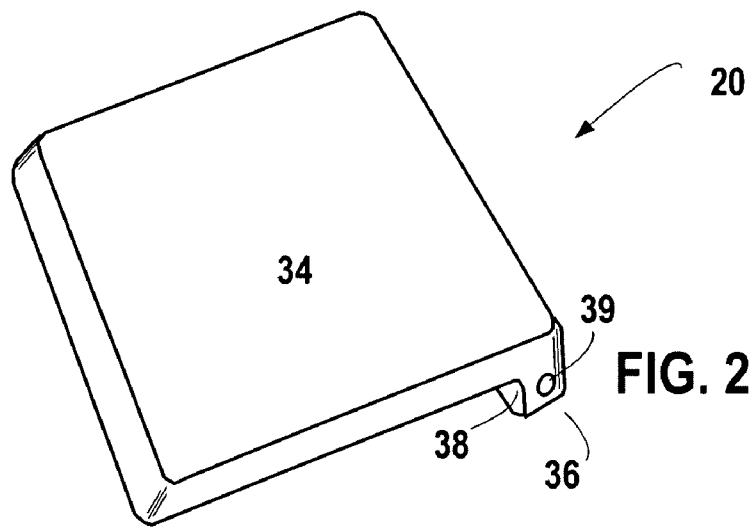
FIG. 2 is a perspective top view of a bucky warmer showing the insulated top of the bucky warmer.

FIG. 2 is a perspective view of the top side of the embodiment of the bucky warmer 20 illustrated in FIG. 1 showing a molded plastic top surface 34 of the bucky warmer 20.

Figure 3:
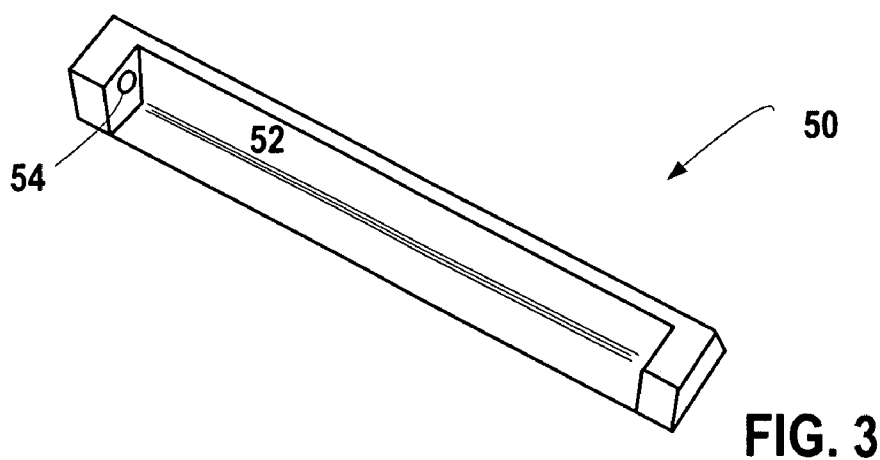
FIG. 3 is a perspective view of a bucky warmer wall bracket showing an electrically powered holder for the bucky warmer.

FIG. 3 is a perspective view of an embodiment of the bucky warmer holder 50 that is configured as a wall bracket. It may comprise a supporting surface 52 that engages the inside surface 38 of the angled end of the warmer 20 in an interferential way to hold the warmer 20 in an upright position. The holder 50 may also comprise pins 54 that serve to further maintain the warmer 20 within the holder 50 when not in use. The warmer 20 and holder 50 are discussed in more detail below with reference to FIG. 5.

Figure 4A:
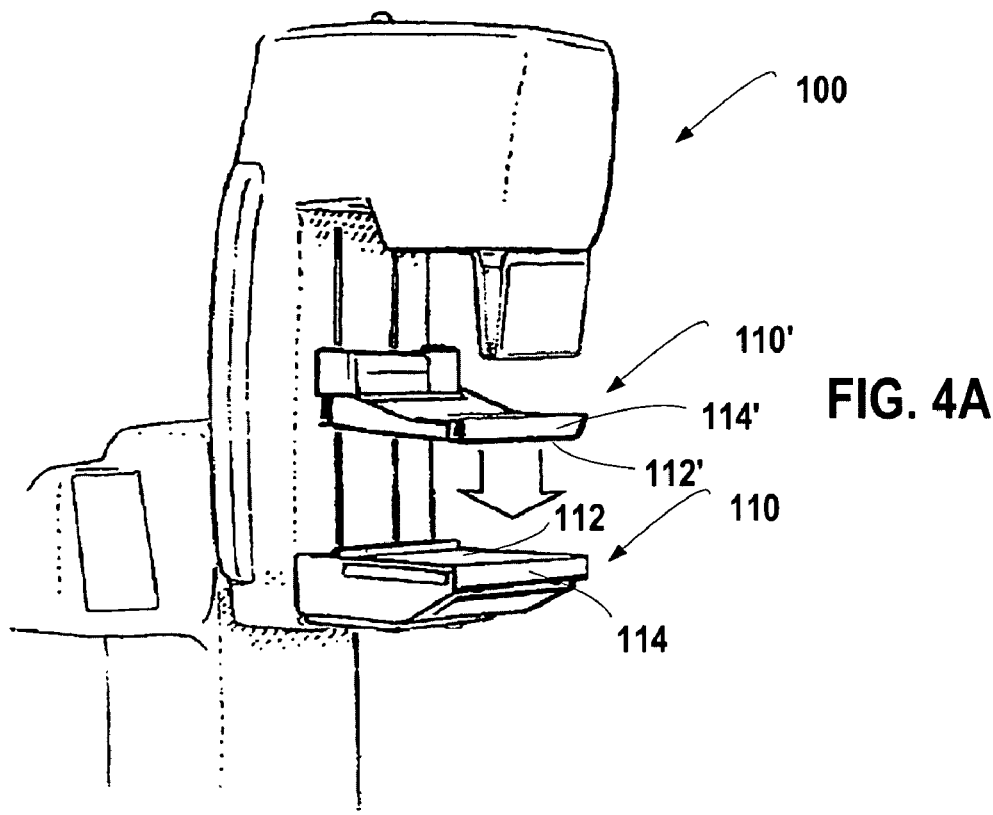
FIG. 4A is a perspective view of an X-ray mammography machine on which the device may be used.
Figure 4B:
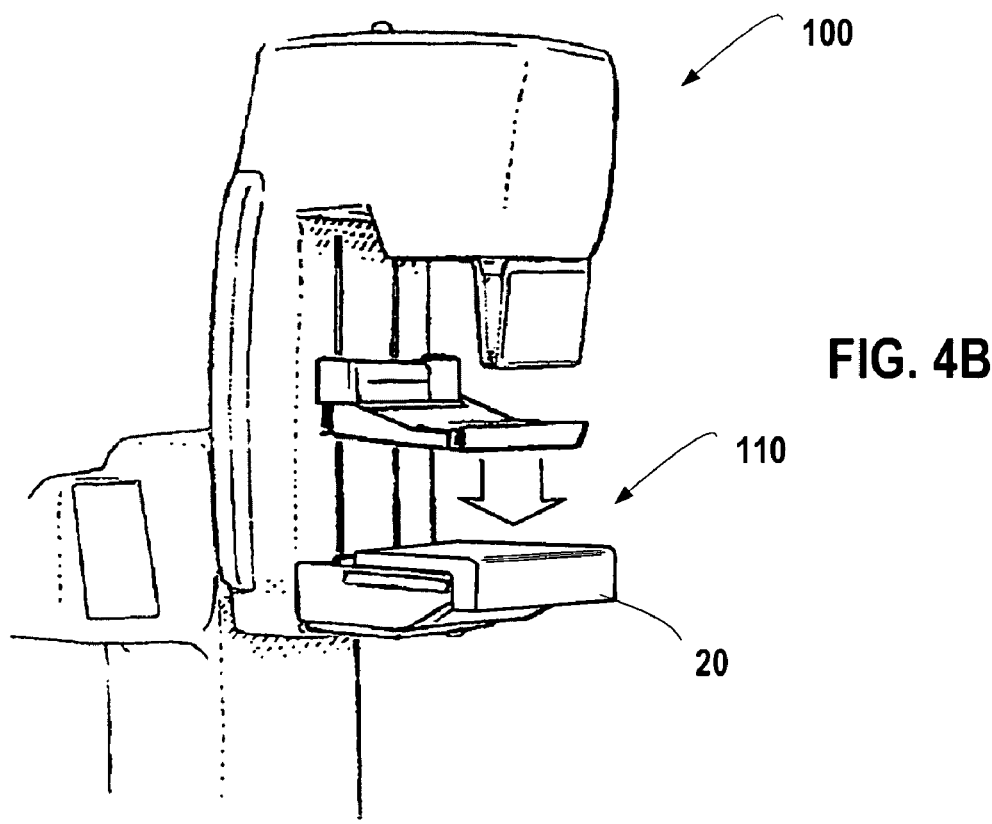
FIG. 4B is a perspective view of the machine in FIG. 4A showing the bucky warmer placed on the bucky.

FIGS. 4A and 4B illustrate the use of an exemplary bucky warmer 20 on an X-ray mammography machine 100. The machine 100 comprises plates which are brought together to compress the breast tissue prior to imaging. The breasts are contacted by a top surface 112 of the bucky 110 and by a bottom surface 112' of a paddle 110'. In the most simple embodiment of the invention, only the top surface 112 of the bucky 110 is warmed by the warmer 20. Additionally, however, in another preferred embodiment, the inside surface 38 of the angled end 36 contacts and warms the side surface 114 of the bucky. Since this side surface 114 would normally contact the chest tissue of the patient, it is desirable to have this surface 114 heated as well.

Furthermore, it is possible to contact one or more surfaces of the paddle 110' as well. If a single warmer 20 is to be used, then the bottom surface of the warmer would be constructed to look like the top surface, and have the corresponding layers and hardware. The warmer 20 could retain its L-shape, or it could be created with a T-shape, in order to accommodate the side surface 114'. A number of configurations could be envisioned, but as a general rule, in these configurations, the insulating layer should be eliminated for portions of the warmer that contact surfaces to be heated.

Although the side surface 114' of the paddle does not generally contact skin tissue, in most instances it would not have to be particularly heated. However, it is possible that in certain configurations and/or for certain individuals, that it would be desirable to heat this side surface 114' as well. Therefore, the warmer 20 could also comprise an additional protruding angled end opposite the one 36 shown in the figures so that, as noted before, the overall cross-section has a T-shape instead of an L-shape.

In operation in these configurations, once the warmer 20 is placed on the bucky 110, the paddle 110' is lowered on to the warmer 20, and once thermal equilibrium is reached, the paddle 110' is raised and the warmer 20 removed.

Alternately, according to the embodiment shown in FIG. 1, a second warmer 20 identical to the first could be used to separately heat the paddle 110'. In this configuration, gravity alone will not hold the warmer 20 to the paddle 110', as it can for the warmer 20 placed on the bucky 110. Therefore, it would be possible to add a strap or clips, possibly with foam rubber or other similar resiliently compressible material to hold the warmer 20 in place against the paddle 110'—any known mechanism can be used to ensure the surface(s) of the warmer 20 contact the appertaining surfaces of the paddle 110'. It is desirable to design all warmer 20 surfaces so that they attempt to maximize contact with the surfaces on the mammography machine 100 that are to be heated.

One of the important aspects is that the bucky 110 comprises sensitive components that can be harmed by an overtemperature condition that in some cases may be as little as 105-110° F., which is why many of the prior art devices that have failed to consider this limitation have led to failure. Prior art warmer systems that do not make great efforts to precisely control the temperature have similarly met with failure.

In the discussion below, the term "surface 112" is used generically to refer to various embodiments of the invention—this description could mean any surface that has been mentioned where it would make sense to do so, for example, it could include the front surface 114 of the bucky 110, the bottom surface 112' of the paddle 110', and the front surface 114' of the paddle 110' where appropriate for the various embodiments.

Advantageously, and according to a method described in more detail below, the proper temperature setting for the bucky warmer 20 can be determined either mathematically or empirically. The thermal mass of the bucky warmer 20 and the thermal mass of the bucky 110 and the paddle 110' can be taken into account as well as the ambient temperature and/or the temperature present on the surface 112 in determining the proper heating temperature for the bucky warmer 20.

In a simple system, a fixed bucky warmer temperature may be used on all systems. In order to ensure that the bucky 110 is not damaged by excessive heat, this may result in a lower plate 112 temperature than that which is optimal. In more sophisticated implementations, unique characteristics related to the machines, as well as variations in the ambient and plate surface temperature can be configured.

Figure 5:
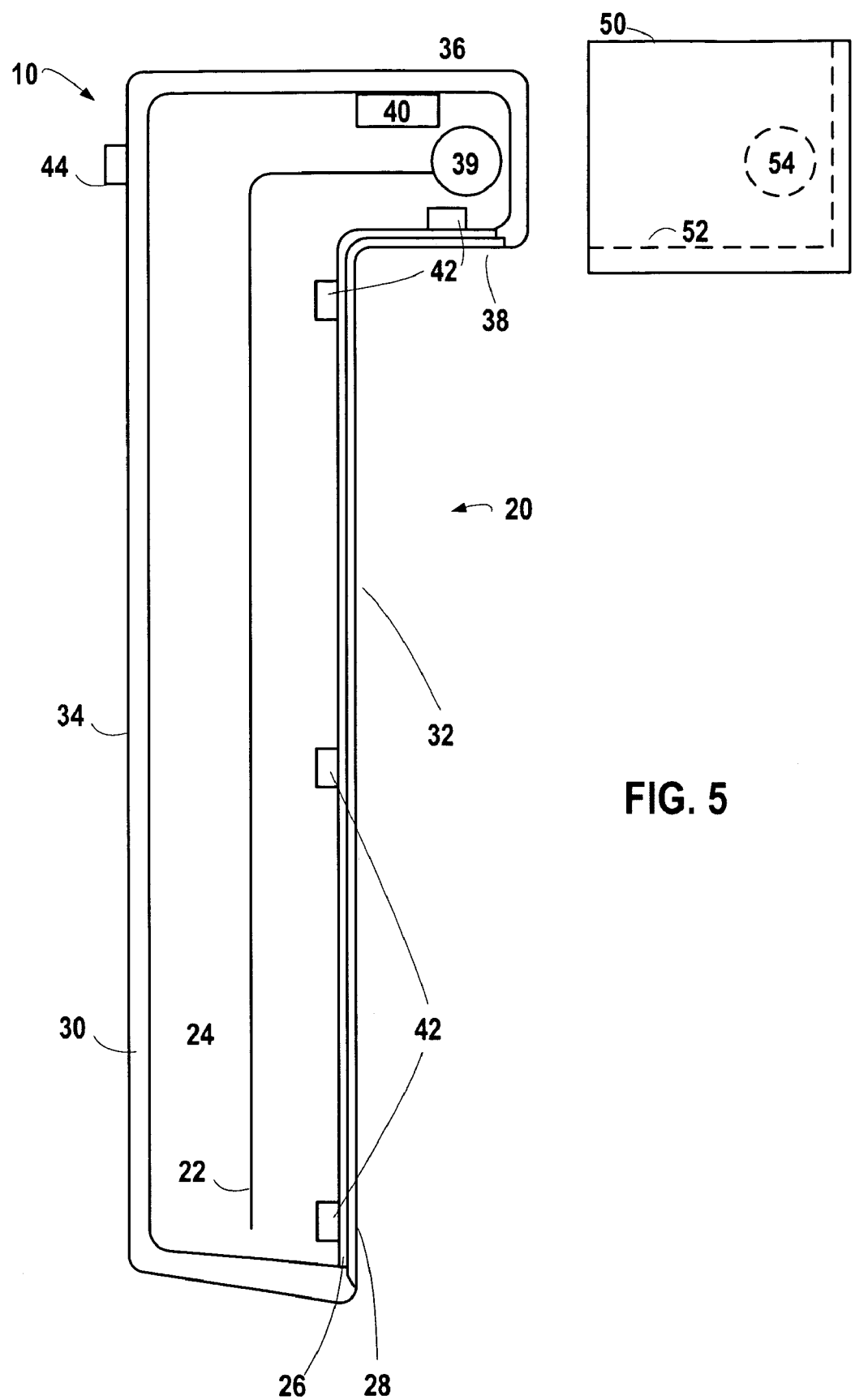
FIG. 5 is a pictorial schematic view of the bucky warmer device and holder.

Referring now to FIG. 5, and in more detail, the bucky warmer system 10 is shown in its upright configuration with the bucky warmer 20 and its holder 50 about to be engaged. In this cross-sectional view, the interior according to an embodiment of the invention can be seen. At the heart of this embodiment is a heating element 22. It should be noted that an alternate embodiment does not need to comprise the heating element, but rather could be passively heated to a desired temperature by an external heater. In the embodiment shown, the heating element could be a single-piece element or could comprise multiple pieces. This heating element could be made of, e.g., Nichrome wire or any other well known heating element.

A filler material 24 is provided that surrounds the heating element. The filler material 24 should have a large thermal mass per unit volume and provide some degree of thermal conductivity in order to uniformly distribute and transfer the heat from the heating element 22 to the bottom surface 32. In one preferred embodiment, rice is used as the filler material 24, since it is inexpensive, generally non-flammable, and comprises a thermal mass that meets the criteria for the warmer 20.

Ideally, the warmer 20 comprises an insulating layer 30 that surrounds the filler material 24 and helps to prevent the stored heat from escaping in a direction that is undesirable, i.e., not in a direction towards the intended surface 112. This insulating layer 30 may actually be the outer tough shell of the warmer 20, or it may be provided below an outer tough shell. This layer may be made of a hard plastic or foam material.

The bucky warmer 20 may also comprise a heat conducting plate 26, such as a metal plate or sheet, that serves to pull the heat from the filler material 24 and direct it toward the bottom surface 32. As mentioned earlier, a thin layer of fabric 28 or the like may be provided to prevent scratching of the sensitive surface 112 of the machine 100.

The bucky warmer 20 ideally comprises a control or processor/control 40 that is used to properly control or regulate the temperature of the device. Although it is possible, according to the invention, to permit a manual control of the temperature (e.g., a user simply turns the heating element on and waits for a temperature display 44 to indicate the correct temperature), in the preferred embodiment, the temperature is controlled and regulated.

The temperature may be sensed by one or a plurality of temperature sensors 42 and read by the controller 40. The heating element 22 is turned on until the temperature sensors reach a desired temperature and then the warmer 20 is shut off. Once the warmer 20 cools to some predetermined threshold, the heating element 22 turns on again. The heating cycle can operate according to well know hysteresis loop cycles.

As noted previously, for a sophisticated system, a wide range of temperature settings can be stored in a memory associated with the processor 40, and a user can possible choose a desired temperature setting form the control panel 44 or possibly chose a device, where the optimum temperature setting for each type of machine 100 can be stored.

The heating element 22, processor/controller 40, and other supporting circuitry, defined as the "thermal circuit" in the bucky warmer 20, is ideally designed for triple redundancy which prohibits/prevents the bucky warmer 20 from an overheating/over-temperature condition that could damage the expensive bucky 110 or cause a burn on a patient. In such a configuration, a regulated power supply and heating element 22 is designed to absolutely limit the maximum temperature, by, e.g., limiting the amount of current and/or voltage to the heating element (presuming some nominal room temperature).

It should be noted that the ideal temperature of the combined bucky warmer 20 and machine surface 112 is the normal body temperature, often cited as 98.6° F. However, this may require the bucky warmer 20 to be heated to a considerably higher temperature, possibly 110° F. or higher, depending on the relative thermal masses. But, of course, care must be taken so that the warmer 20 will not overheat and damage the bucky 110.

In a simplistic embodiment, a bimetal temperature control element maintains a constant 85° F. to 95° F., and other failsafe mechanisms, such as a fusible link that opens and disables the electrical circuit if the unit exceeds, e.g., 115° F. could be utilized. In more complex models, the temperature could be fixed at a single temperature by a simple thermostat initially set at the factory, or a thermostat having an adjustable setting could be used, where the adjustment could be done through a simple knob or other control device.

It is also possible to use redundant controls or processors 40 to prevent overheating. In the multiple temperature sensor 42 embodiment, a cutoff threshold can either be based on an average value or some maximum value for a single or grouping of the sensors 42. Finally, the display 44 can be used to indicate an over-temperature condition. It may be possible to provide a separate over-temperature LED in a simple version, and perhaps some sort of flashing indicia or just a temperature readout that might indicate a potential problem on a more sophisticated display 44. This would be an indication to a radiological technologist (RT) that he or she should NOT use the bucky warmer 20 at that time.

In a preferred embodiment of the invention, redundant mechanisms could be used alone or in combination to ensure that an over-temperature situation cannot be reached—these could be used alone or in any combination: 1) limited power supply—the power supply is designed to limit the current flowing to the warmer 20 so that it cannot heat beyond a certain temperature; 2) temperature sensor—the sensor can detect an over-temperature condition and provide an output that can be utilized to control the amount of power reaching the heating element; and 3) thermal fuse—the thermal fuse can be provided to disconnect the heater in the event that an over-temperature condition exists.

In a preferred embodiment, the power components are medical grade for use in health care facilities, meeting UL and CE directives.

Power may be provided to the bucky warmer 20 via contact points 39 that are located on opposite sides of the warmer 20. In a preferred embodiment, the contact points 39 are recessed metallic connectors that mate with protruding metallic pins 54 of the holder, and the pins 54 may be spring loaded to bias the pins into the recessed contact points 39 when the warmer 20 is mounted in the holder 50. In this configuration, advantageously, the power connection then may also serve to further secure the warmer 20 in the holder.

It should be noted that the pins 54 do not have to be spring loaded, but could be implemented as screws or any other similar mechanism that would permit protrusion. However, the spring loading permits easy attachment and removal of the bucky warmer from the holder 50. Alternately, the male/female nature of the pins 54 and recessed contact point 39 could be reversed so that, e.g., the recess is on the holder 50 and not the warmer 20. Such a mating holding system could be implemented without these being the power connection, and that the power connection could take any form of plug-and-socket form or any form of mating contact configuration as is known in the art.

Ideally, the holder can plug into a standard U.S. wall socket and operate on 110V (or 220V for a European configuration), but any operating voltage is possible. As an additional safety measure, the power supply cable can be current limited to prevent overheating or damage. The wall hanging bracket 50 can be attached to a wall or the radiation shield located near the mammography machine 100 using screws, a supplied Velcro strip, or any other fastening mechanism. The bucky warmer wall bracket may utilize an on/off switch for heating circuit control. Spring-loaded contact points are recessed for easy attachment and removal of bucky warmer from wall bracket.

It is also possible, in an embodiment of the invention, that the warmer 20 itself contains its own rechargeable power source, such as batteries. The advantage to this approach is that the warmer 20 need not begin cooling the moment it is removed from the holder 50, although this configuration removes an element of the fail-safe in that it then becomes possible for the warmer 20 to overheat even after it has been removed from the holder 50. Nonetheless, it should be possible to implement adequate safeguards for this configuration, such as through the use of known redundancy techniques.

However, in the preferred embodiment, the power supply is provided by the holder 50. The heating element 22 is designed to heat the filler 24 to provide the heat to the mass of the bucky warmer 20. This allows the bucky warmer 20 to be powered and attain and maintain the desired temperature while connected to the holder 50. After the desired temperature is attained in the bucky warmer 20, it is then disconnected from the holder 50 and placed on the bucky surface 112 of the mammography x-ray machine 100.

The large heat reservoir stored largely in the filler 24 is then slowly dissipated into the bucky 110 and, optionally, paddle 110' of the mammography x-ray machine 100 to provide the skin contact comfort temperature level required. The bucky warmer 20 will normally reside on the wall bracket 50, and will be removed from it and placed on the bucky surface 112 of the mammography x-ray machine 100 a few minutes before the arrival of each patient, or in whatever timeframe is deemed proper to perform the heating. In this embodiment, there is no need to have cords or wires connected to the bucky surface 112 of the mammography x-ray machine 100 in an effort to warm it, and yet a controlled temperature can be provided.

The layer of foam insulation 30 in the bucky warmer 20 improves the unit's efficiency by reducing heat lost to the outside air. The outer surface of the bucky warmer can ideally be designed to be easily cleaned by wiping it with, e.g., a 5% alcohol solution or any other form of mild disinfectant.

Configuration—Calibration

As noted above, in an idealized situation, the surface will be exactly at body temperature, i.e., 98.6° F. when it contacts the skin. However, in order to bring these surfaces from room temperature to this ideal temperature, the bucky warmer 20 should be heated to a higher temperature so that when it contacts the colder bucky 110 (at room temperature), once the heat transfer has occurred between the warmer 20 and the bucky 110 and paddle 110', the combined temperature is at body temperature.

However, as also noted above, the bucky 110 contains sensitive imaging equipment that can be damaged by excessive heat, which may be as little as 105° F. Therefore, utmost care should be taken when determining the temperature setting for a given machine. Although precise mathematical calculations could be used to determine such settings, it is much easier to determine these values empirically by experimentation.

In the simplest approach, the bucky could always only be heated no warmer than a maximum value tolerated by the bucky. Thus, if the bucky temperature limit was 105° F., then this would be the maximum temperature set for the warmer 20. However, if an optimum temperature was desired, one could allow the bucky 110 to stabilize at room temperature, and then begin by heating the bucky warmer 20 to a particular initially low temperature, e.g., 85° F., contacting the bucky 110 with the warmer 20, and measuring the ultimate temperature once it has stabilized. The process is repeated, slowly increasing the temperature of the warmer in, e.g., 3° F. increments, until the optimum combined warmer 20 and bucky 110 temperature is achieved. This ideal warmer 20 temperature would then be noted as the recommended setting for a particular model of bucky at a particular room temperature.

This process could be repeated for a number of different room temperature settings, for example, in 3° F. increments as well. In this way, a table could be made containing ideal bucky warmer 20 temperature settings for a particular model of bucky 110. In this way, the bucky warmer can be accurately calibrated and the optimum comfort factor determined without threatening the sensitive components of the bucky 110.

As an alternative, instead of room temperature settings, the actual surface temperature of the bucky 110 itself could be used. Although this would be a more complex procedure, and require the presents of a temperature sensing device on the bucky 110 itself, it would permit the use of the bucky warmer even when the bucky 110 is warmer than room temperature due to recent use.

Operation

The following description is an example of how the system 10 could be utilized in a practical setting.

At the beginning of the work day, the RT (radiologic technologist): a) places the bucky warmer 20 into the wall bracket/holder 50; b) turns the on/off switch on the wall bracket 50 to ON; and c) allows approximately, e.g., 15-20 minutes for the bucky warmer to fully heat to it's specified, safe temperature. This time frame is exemplary, and could be different depending on what heating elements are used, the control system, the filling material, etc. An initial heating of the bucky warmer 20 will take longer than subsequent warmings when the warmer 20 is above room temperature.

Mammography clinics report providing up to as many as 4 mammogram procedures per hour. Thus, once the bucky warmer 20 is initially heated and used, it should be immediately returned to its wall bracket 50 after use and quickly re-warmed for further use.

When the bucky warmer 20 is fully heated, and, in the exemplary embodiment using the LED device, it's LED indicator 44 indicates a temperature within an ideal predetermined range. This could be, in a simplistic and safe setting, a range of 85-95° F. At this point, the RT lifts/removes the bucky warmer 20 from the wall bracket 50 and places it on the bucky cover surface 112 of the mammography X-ray machine 100. This removal from the bracket 50 process is designed for ergonomic ease for RTs and may be done with one hand, if desired, due to the advantageous monolithic construction of the bucky warmer 20 according to an embodiment. The materials used can be relatively light (e.g., the molding, rice, and thin sheet metal conductor) so that it can be handled easily with one hand.

The bucky warmer 20 remains on the bucky cover surface 112 of the mammography X-ray machine 100 until the patient arrives in the room to begin their procedure. As the patient approaches the X-ray machine 100, the RT removes the bucky warmer 20 and replaces it in the wall bracket 50. It is further possible that the paddle 110' is also brought down so that it's bottom surface 112' and optionally its side surface 114' contact the warmer 20 as well, thereby warming all surfaces that will come into direct contact with the patient.

Now, placed back in the wall bracket 50, the bucky warmer's 20 temperature sensor(s) 42 senses its current temperature and re-warms the device to the ideal temperature.

The RT positions the patient for the procedure on the X-ray machine 100, whose exposed skin is in contact with the surface of the bucky cover 112 during the procedure.

This warming of the bucky cover surface 112 from room temperature to within a few degrees of normal body temperature, considerably enhances patient comfort and relaxation.

Research indicates that mammography images are significantly improved/enhanced when the patient is relaxed and comfortable, resulting in breast tissue being more fully compressed. Removing such room temperature equipment cold stress to exposed skin contributes significantly to patient comfort/relaxation and improved mammography X-ray images.

When the bucky warmer 20 is no longer needed (e.g., at the end of workday), the RT replaces the bucky warmer 20 into the wall bracket 50, turns the wall bracket switch to OFF and allows the bucky warmer 20 to cool completely.

First Alternate Embodiment

Figure 6:
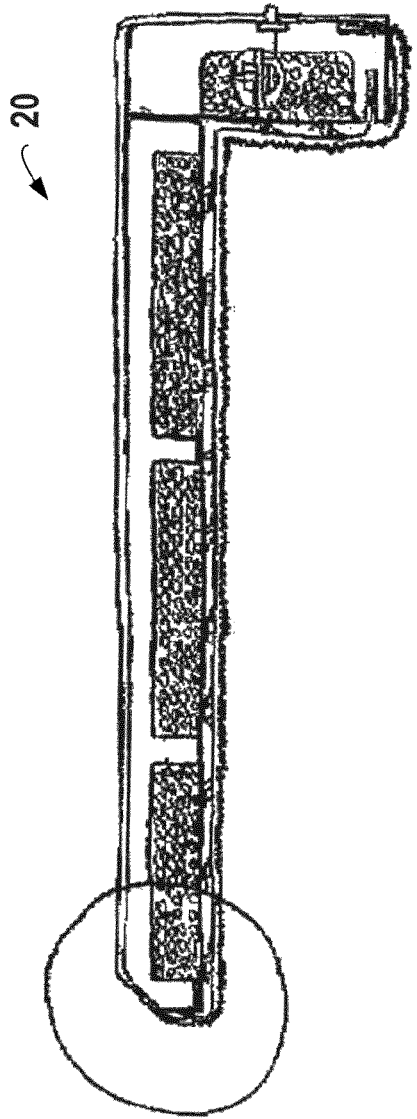
FIG. 6 is a cross-sectional view of the warmer according to another embodiment of the invention.
Figure 7:
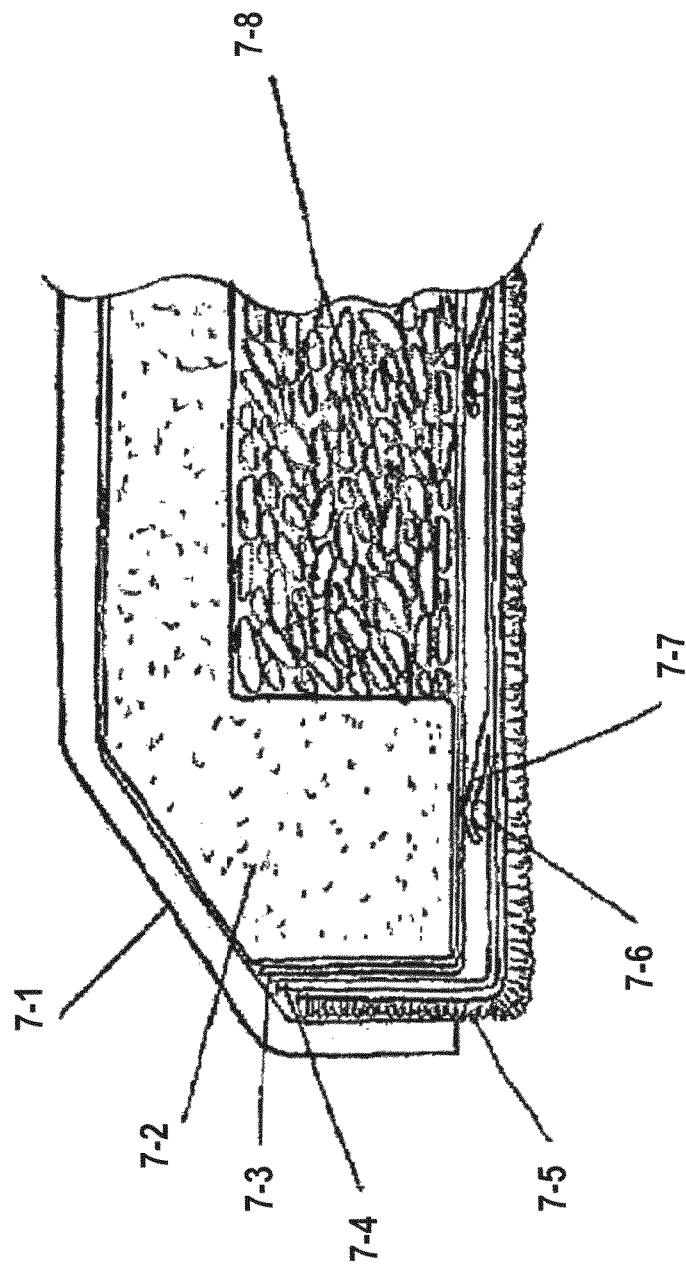
FIG. 7 is a cross-sectional view of an end portion of the embodiment shown in FIG. 6.

According to an additional practical preferred embodiment, FIG. 6 illustrates a cross-section view of the warmer 20 according to this embodiment. FIG. 7 is a magnified view that illustrates one configuration for the warmer. Accordingly, a plastic outside cover 7-1 is above a foam insulation layer 7-2. A material having a substantive thermal mass 7-8 is provided within pockets of the foam insulation 7-2. A heating element 7-6 is provided that is associated with a heating element support tab 7-7. An adhesive backed seal sheet 7-3 is further provided. A heater wire support sheet 7-4 is provided to support the heating elements in its operational and storage configurations. In this embodiment, the outer surface on the bottom of the warmer 20 is provided by a flocked cloth cover 7-5 that is non-abrasive and will not harm the surface of the bucky that it comes in contact with. A further thermally conductive layer can also be provided.

Figure 8:
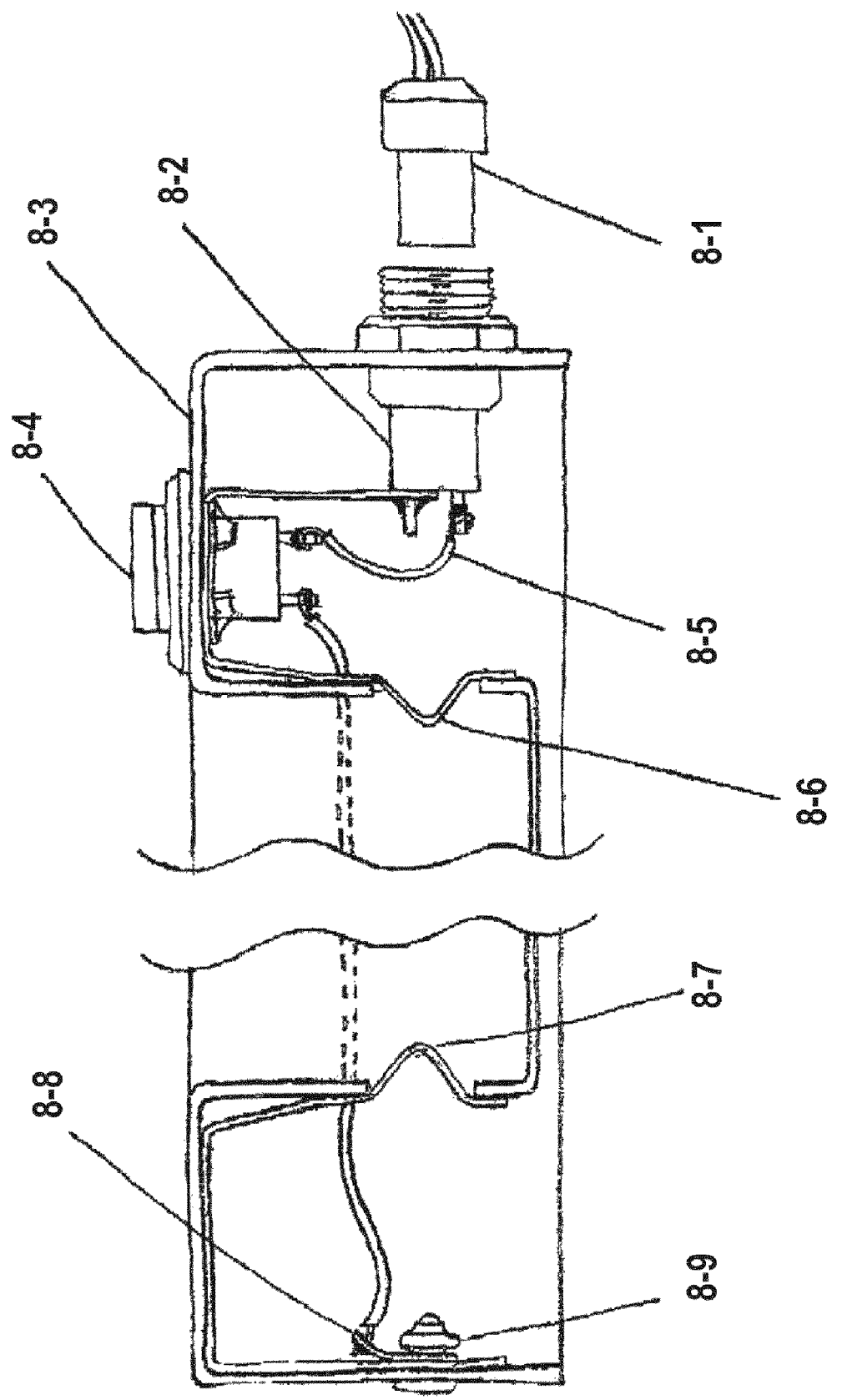
FIG. 8 is a cross sectional view of an exemplary wall mounting bracket assembly.

FIG. 8 shows an exemplary embodiment of the wall mounting bracket assembly, which has a power input 8-1 (e.g., for a 15 VDC power input), a power input socket 8-2, a wall mount plastic housing 8-3, an on/off switch 8-4, a positive power lead 8-5, negative spring contact 8-6, a positive spring contact 8-7, a positive lead terminal 8-8, and a positive terminal securing rivet 8-9.

Figure 9:
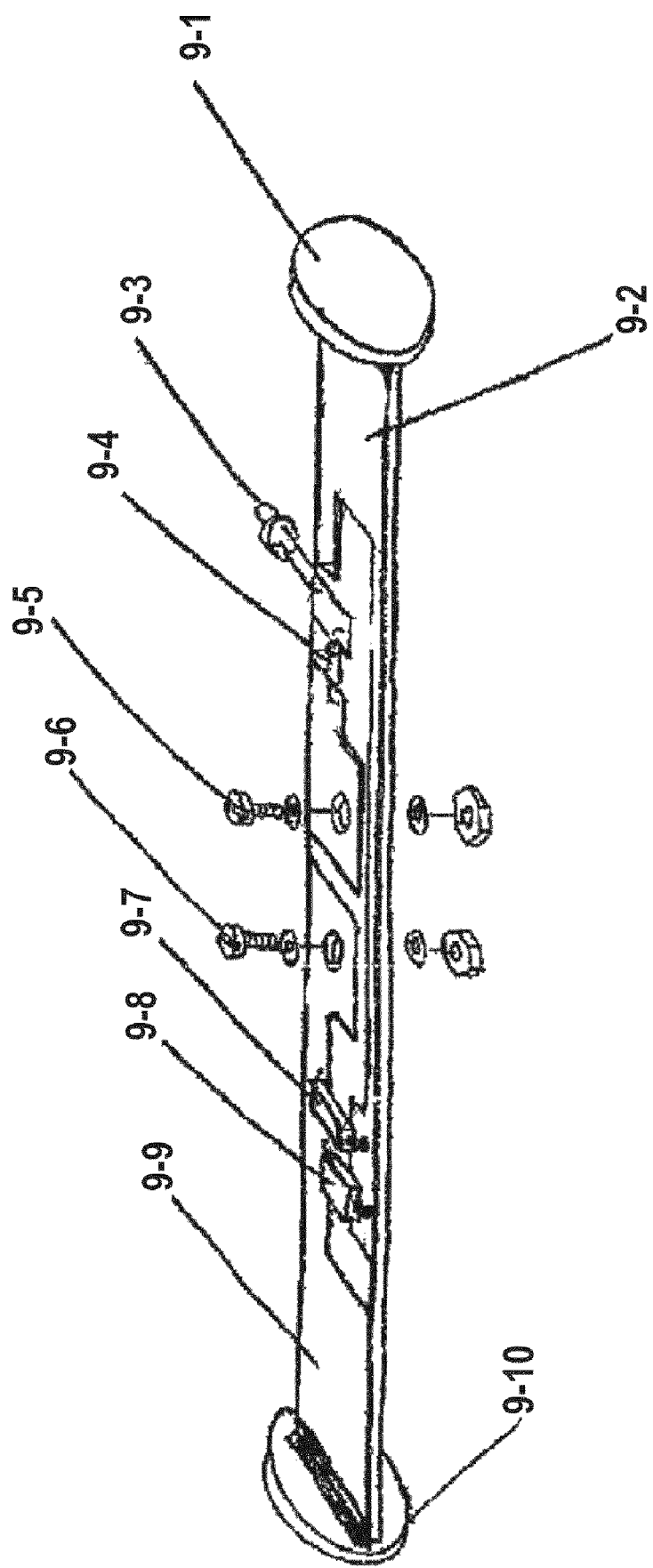
FIG. 9 is a perspective view of a control and contact PC board.

FIG. 9 shows an exemplary control and contact PC board. Accordingly, positive 9-10 and negative 9-1 contact disk are shown adjacent to a positive 9-9 and negative 9-2 printed circuit board contact surface. An indicator in the form of a temperature indicating LED 9-3 is also shown. A reverse polarity protection diode 9-4 is provided in order to prevent the device from exceeding operating parameters. A negative 9-5 and positive 9-6 heating coil securing screw are also provided, as is a temperature control chip 9-7 and thermal fuse 9-8.

Figure 10:
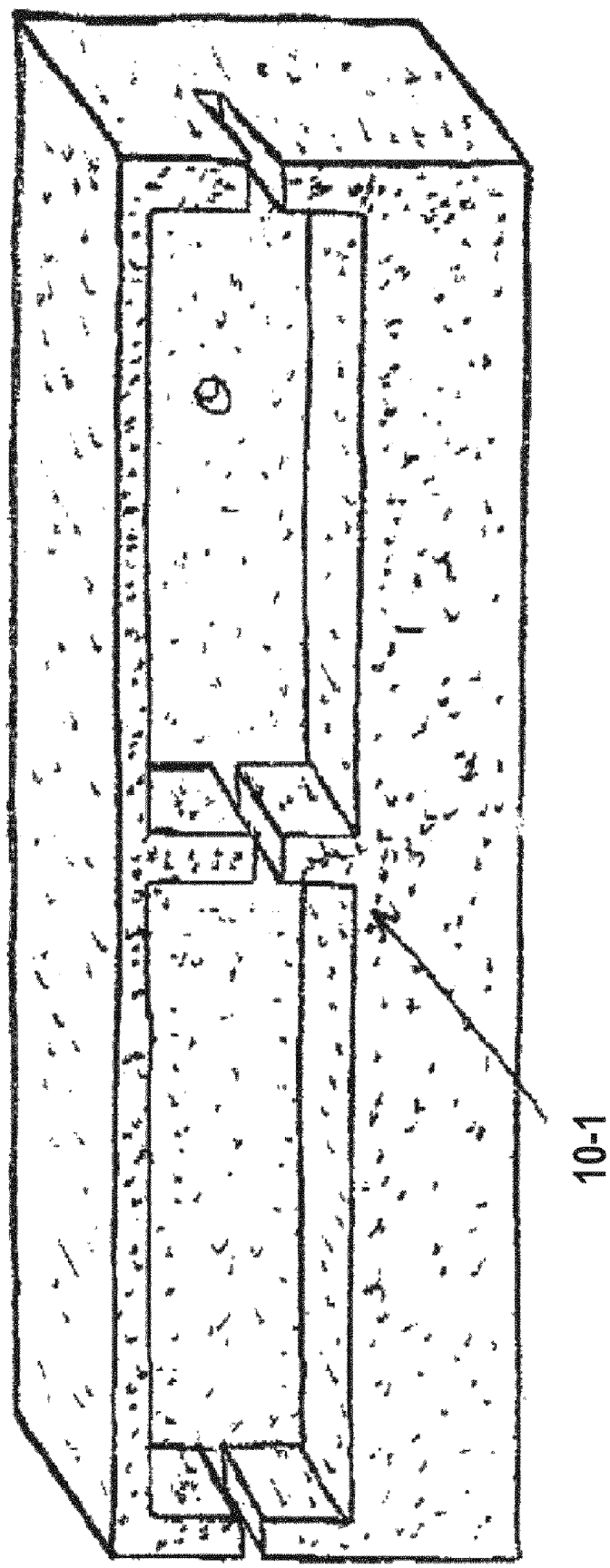
FIG. 10 is an exemplary bucky insulation block/filler.

FIG. 10 shows an example of a section of the insulating block 10-1, showing pockets.

Figure 11A:
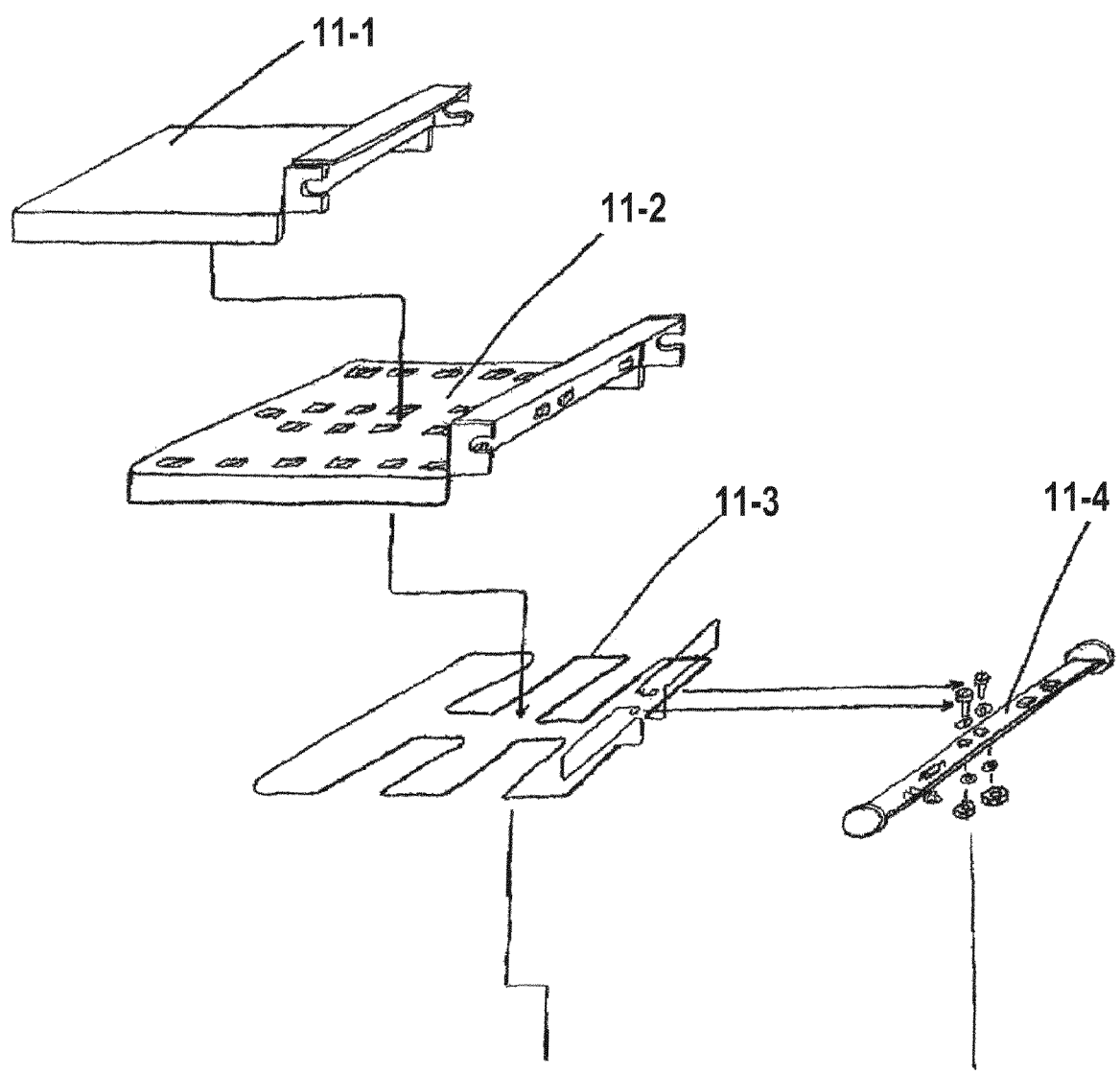
FIGS. 11A, B is an exploded view of the bucky warmer assembly according to the embodiment of FIG. 6.
Figure 11B:
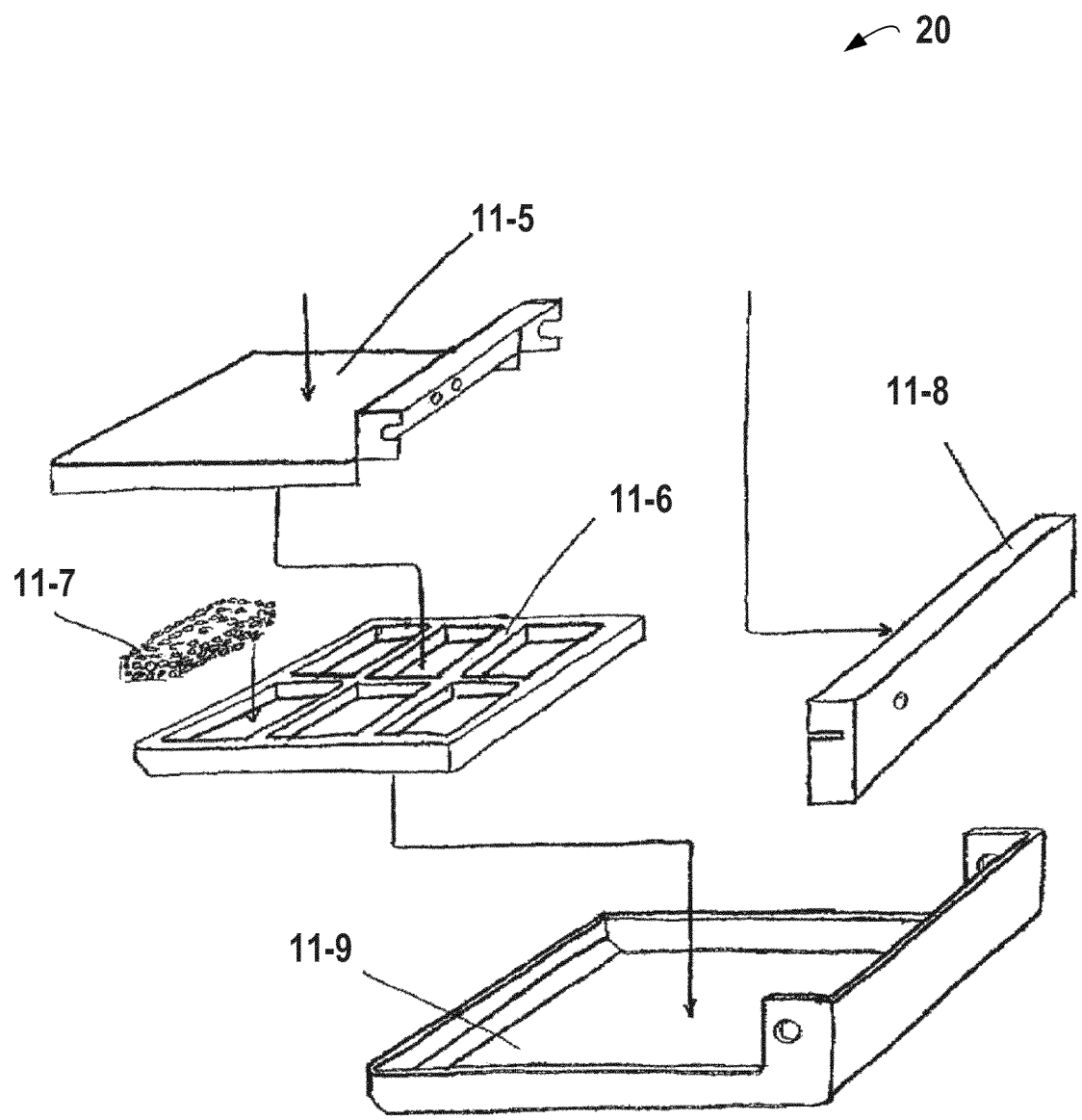

FIGS. 11A, B represent an exploded view of the bucky warmer assembly 20, illustrating shows the flocked cover 11-1, the heater wire support 11-2, the heating wire 11-3, the heater contact and temperature control circuit 11-4, the adhesive backed seal sheet 11-5, the foam insulation horizontal section 11-6, thermal inertial/mass beads 11-7, a vertical section for the foam insulation 11-8, and a plastic outside cover 11-9

Figure 12:
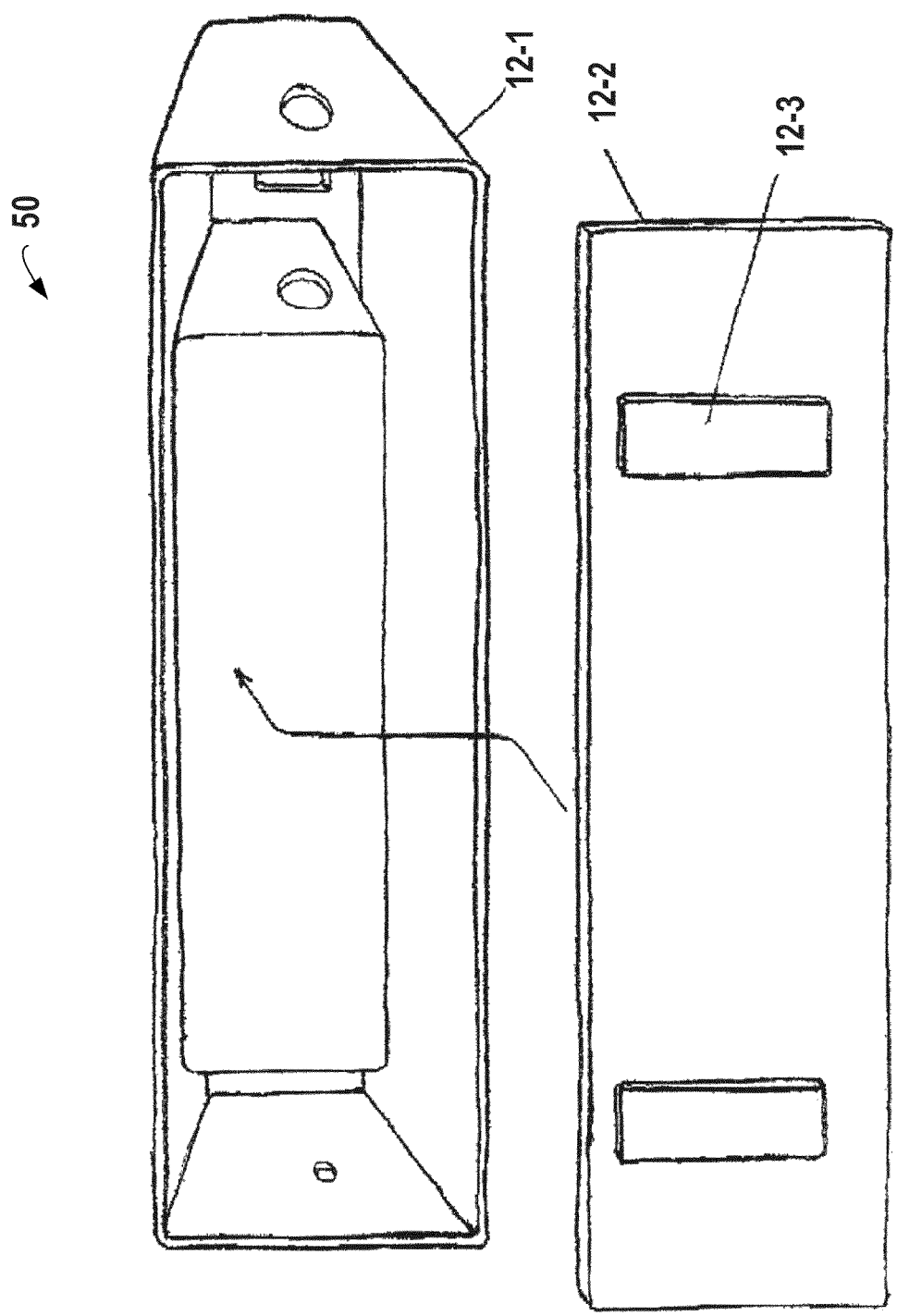
FIG. 12 is a rear perspective view of an exemplary holder.

FIG. 12 shows a back view of an exemplary holder 50 which is a wall bracket assembly, which comprises a front section plastic housing 12-1, a rear cover 12-2, and double face tape 12-3. Of course, the mounting mechanism could be any form of well known fastening mechanism, such as wall-mounted screws, nuts and bolts, glue, magnets, Velcro, etc.

Figure 13:
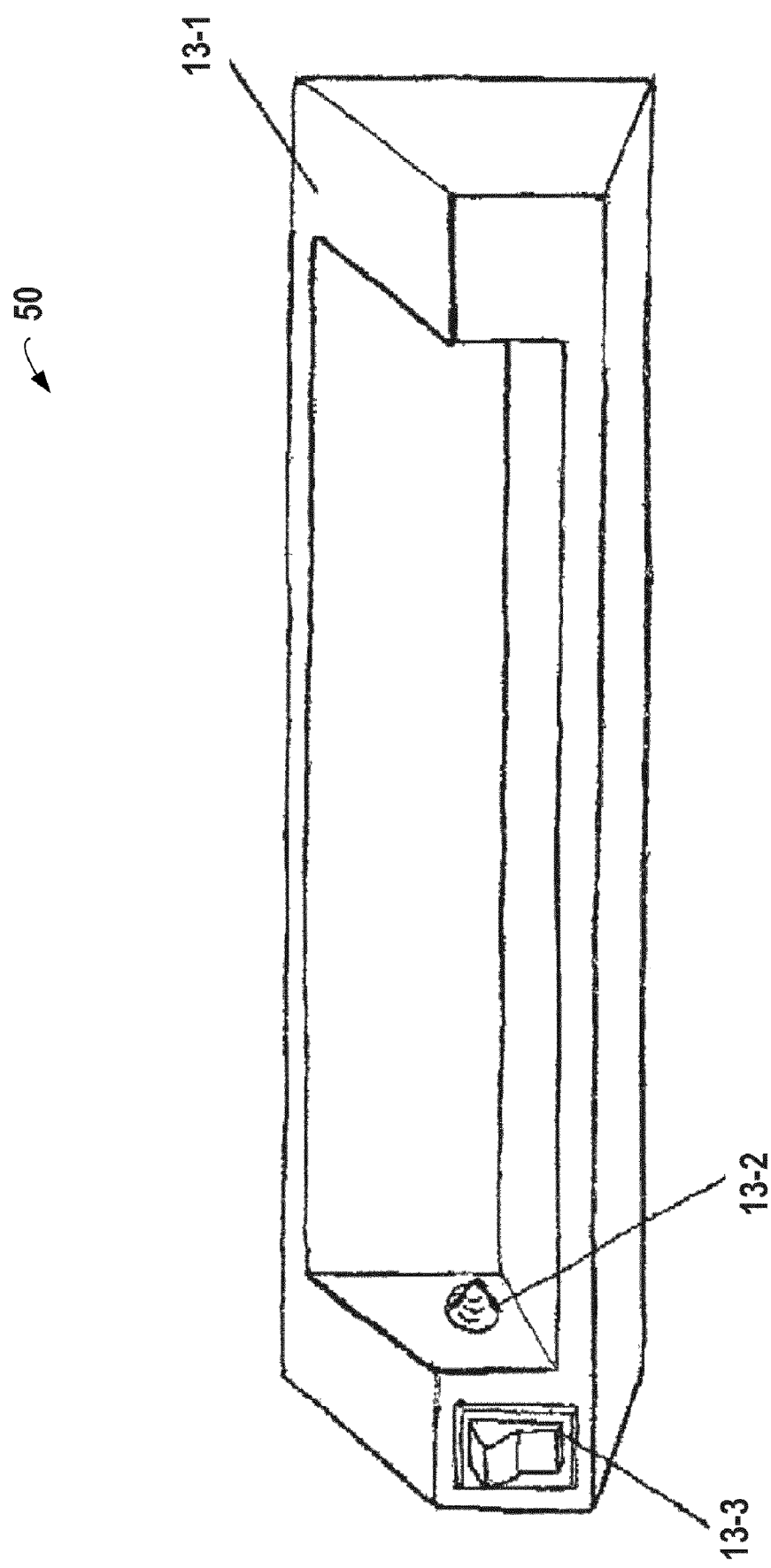
FIG. 13 is a front view of an exemplary holder.

FIG. 13 illustrates a front view of the exemplary holder 50 of FIG. 12, and includes the plastic housing 13-1, the electric contact terminal 13-2, and the on-off switch 13-3.

Figure 14:
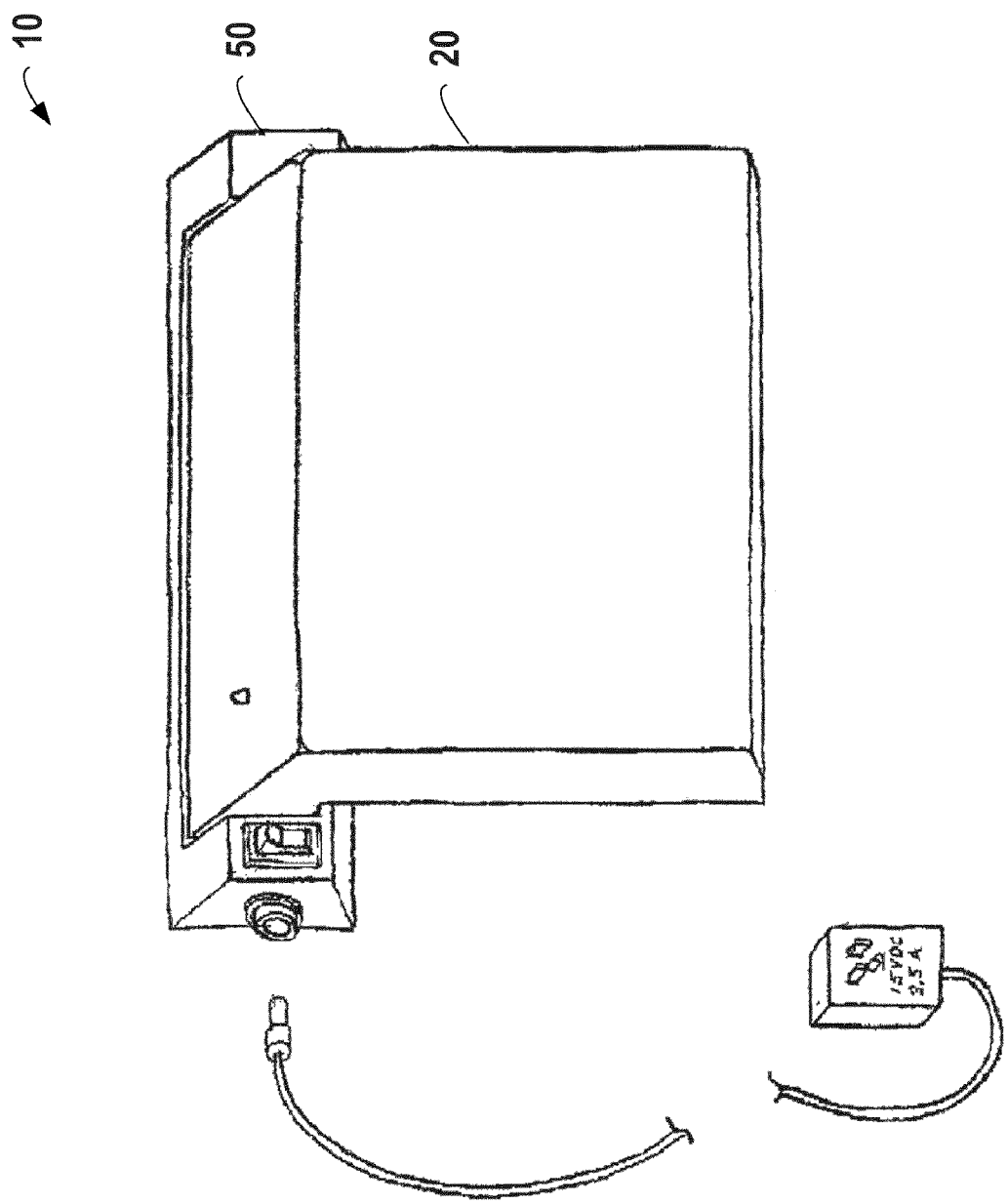
FIG. 14 is a front perspective view of the combined warmer system according to the embodiment illustrated in FIG. 6.

Finally, FIG. 14 shows an assembled warming system 10 with the warmer 20 mounted in its holder 50.

Overall, according to a preferred embodiment, the warmer 20 is approximately 10" wide and 2.5" thick, including the L-portion of the edge, and the holder is approximately 11.5" long and has a cross sectional area of between 1"×1" and 2"×2". These dimensions can be easily modified by one of ordinary skill in the art to accommodate various bucky and paddle configurations.

Second Alternate Embodiment

Figure 15:
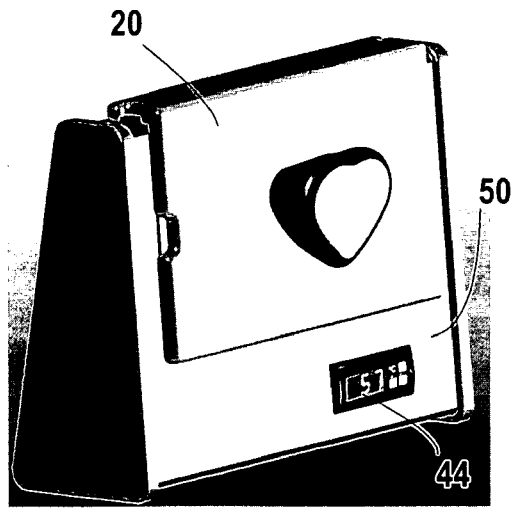
FIG. 15 is a perspective view of an alternate embodiment in which the heating unit is a part of the holder.

FIG. 15 illustrates another embodiment for warming one or more surfaces of a diagnostic or therapeutic instrument, such as a mammography machine in which the bucky warmer (or mobile heat transfer pad) 20 is a passive heating element that sits on a holder 50, which can serve as a pedestal, in a detachable manner wherein the holder comprises the heating unit 43. The warmer 20 can simply be held in the holder 50 due to gravity and the interfering fit of respective surfaces of the warmer 20 and holder 50, but can alternately utilize known fastening or holding mechanisms, such as clips, latches, locks, Velcro, and the like.

Figure 19:
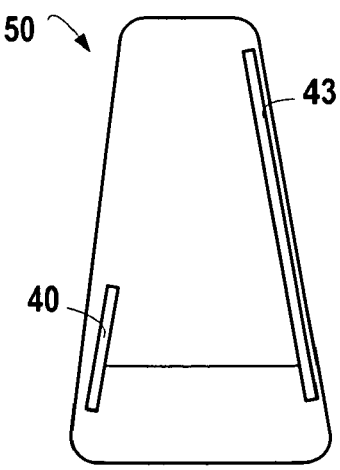
FIG. 19 is a side pictorial view of the holder illustrating the heating unit and control.
Figure 20:
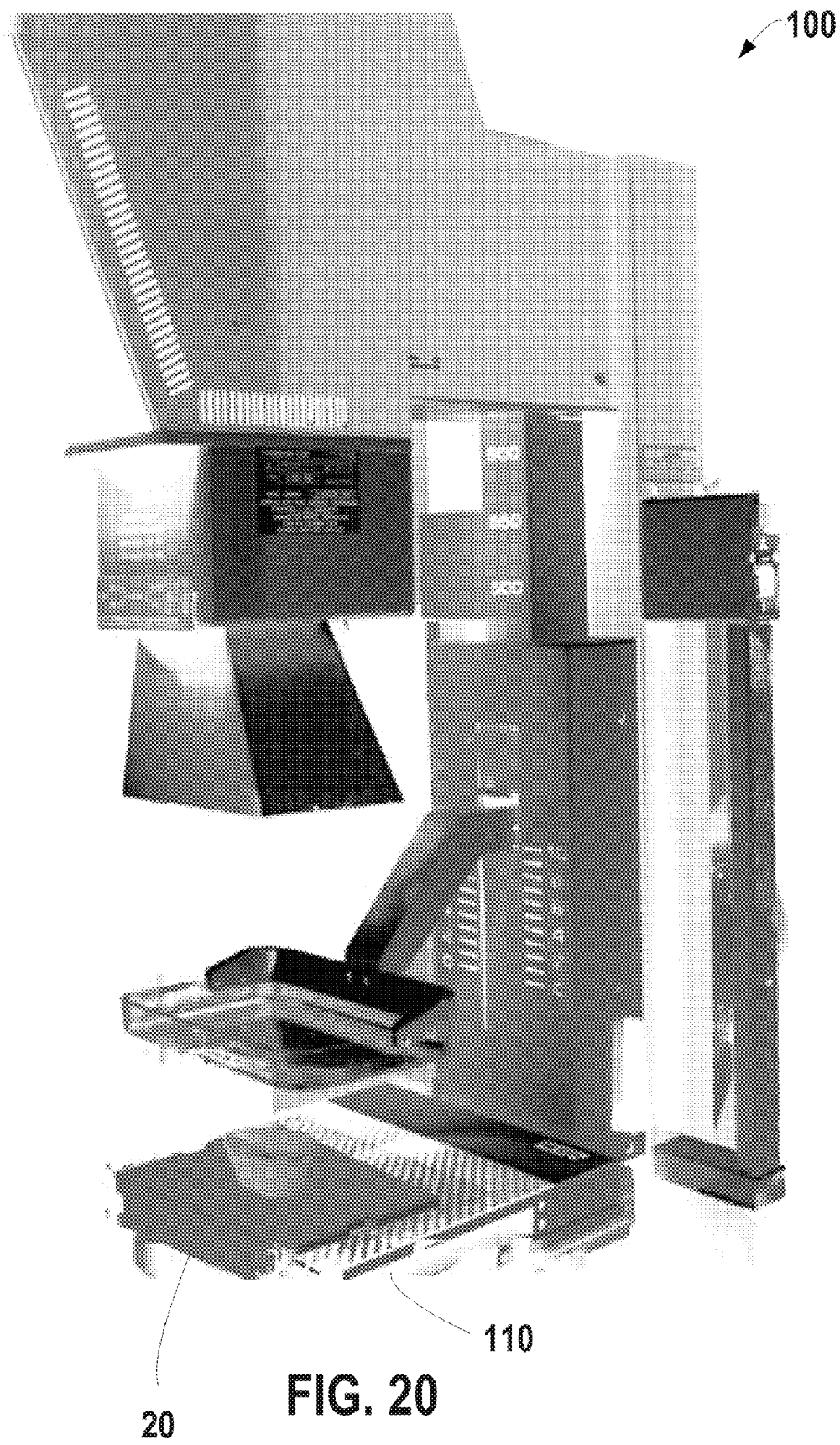
FIG. 20 is a perspective view of the heating pad in the embodiment shown in FIG. 15 in use on a mammography machine.

The heating unit 43 (see FIG. 19) can comprise any of the above-described constructions, such as Nichrome wire and the like. The holder 50 can be configured to accept a standard electrical input from the power grid (e.g., 120v at 60 Hz, or 240v at 50 Hz), or can be configured to run off batteries. The control circuitry 40 includes circuitry for precisely controlling the temperature to the heating unit 43, and can include a thermostat that will permit precise control the temperature to within a degree or two, e.g., of the 104° F. maximum grid temperature requirements of the bucky (note that for digital devices, the maximum allowable temperature could be body temperature, i.e., 98.6° F.). This is important, as noted above, because overtemperature conditions on the bucky itself can damage sensitive electronics and imaging hardware found in most medical imaging equipment of this type. As a failsafe mechanism, the limit temperatures can be preset by the manufacturer to ensure compliance with temperature requirements.

The holder 50 body can comprise filler material having additional thermal mass that can help the holder 50 retain heat and more quickly bring the warmer 20 up to the desired temperature. This thermal mass could act as a further heat reservoir that can be heated even when the warmer 20 is detached from the holder. Alternately, or in addition, a thermal insulating cover could be provided to the holder 50 to help retain heat when the warmer 20 is removed from the holder 50.

As indicated in the figures, a temperature indicator 44 is shown on the holder 50 itself, although this indicator could be provided on the warmer 20 alternately or additionally, and can be implemented either passively (such as via a bi-metallic-strip-based thermometer or thermochromic materials that indicate temperature by color) or actively (such as an LED or LCD display). An active temperature indicator 44 located on the warmer 20 itself would require a power source, such as batteries, to be included in the warmer.

Figure 16:
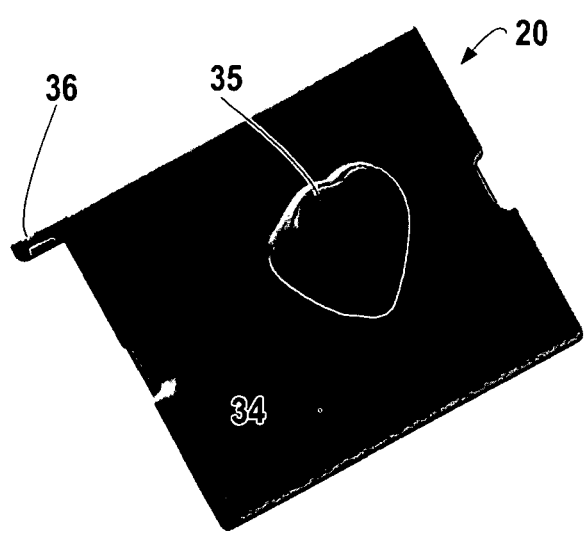
FIG. 16 is a top perspective view of a the heating pad for the embodiment shown in FIG. 15.
Figure 17:
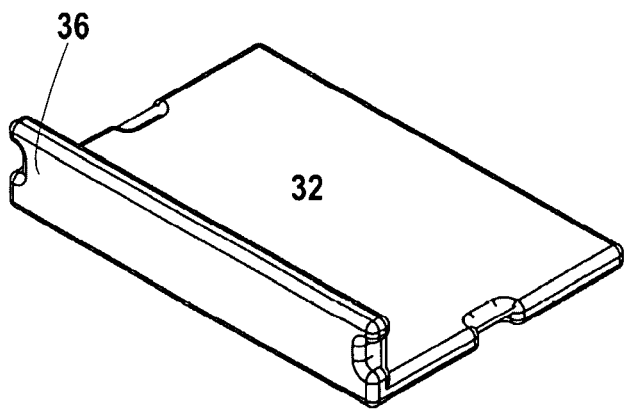
FIG. 17 is a bottom perspective view of the heating pad shown in FIG. 16.
Figure 18:
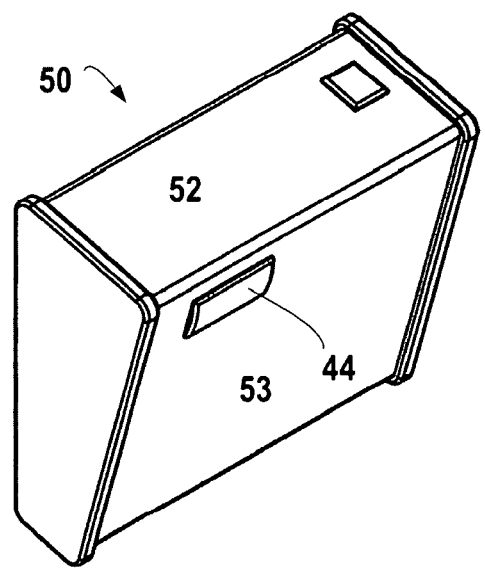
FIG. 18 is a bottom perspective view of the holder.

FIGS. 16 and 17 show a warmer 20 according to this embodiment. The warmer 20 comprises a similar L-shaped body to the embodiments described above, but can be designed to be much thinner since it is passively heated and therefore does not require the extensive heating elements as described in the previous embodiments. The warmer 20 can comprise a metal (e.g., aluminum) plate (e.g., 8-gage, 0.1285" thick), or thicker, or other material having a thermal mass that can serve as a heat reservoir, which can comprise the same L-shape as the warmer itself. The relative thermal masses of the warmer 20 and the element to be heated, such as the bucky, can be determined, and the appropriate temperature for the warmer 20 can be calculated or determined empirically to implement a precise warming temperature on the surface to be heated.

Tables could be developed that provide a proper heating of the warmer 20, based on: 1) a particular type of bucky (each different type of bucky would have a different thermal mass), and 2) the ambient temperature of the bucky prior to warming. In this manner, the final temperature of the bucky could be very precisely controlled to provide maximum warming benefit, while at the same time protecting the electronics of the bucky itself from an overtemperature condition.

Although the size of the warmer 20 can obviously be varied to accommodate various size buckys, the preferred embodiment can be implemented with dimensions of 6.5"×10"×1.5", which should be suitable for the vast majority of buckys currently available.

Advantageously, this design can provide for a rapid heating of the warmer 20, which permits a high cycle use (i.e., low turn-around time for reheating). The bottom surface 32 of the warmer 20 is generally designed to have a large contact surface with a heating surface 53 of the holder 50 to further effect a rapid heating of the warmer 20. The heating surface is ideally made of any heat-conducting material that can easily and evenly transfer heat from the heating unit 43 of the holder to the bottom surface of the warmer 20. The bottom surface 32 contacts the surface of the bucky or other medial device surface in operation.

The warmer 20 may comprise a thin laminate of a heat-conducting material affixed to those surfaces contacting the bucky, and the metal plate may have a substantially thicker heat insulating material on its opposite surface 53 (e.g. those surfaces not in contact with the bucky) to help heat from escaping from the top surface, and helping to prevent an unnecessary loss of heat. The warmer may comprise an ergonomic handle 35 that can be used to transport the warmer to and from the holder 50 and to facilitate placement either on the bucky surface or within the holder 50. Suitable materials could include urethane-based materials.

Advantageously, the two coating material layers, the conducting material layer and the insulating material layer, may be sealed at their edges, forming an airtight enclosure for the warmer 20 that can seal it against external contaminants. This can be important if cleansing by immersion in water or other cleaning fluid is desired.

As with the other embodiments, the present embodiment could be designed with a T-shaped cross-section instead of an L-shaped cross-section so that both the upper surface of the lower bucky unit and the lower surface of the upper unit can be simultaneously heated. In this configuration, the warmer 20 would comprise two conductive layers instead of a conductive layer and an insulating layer, and the handles 35 would be located on the sides of the warmer 20. The holder 50 could be configured to comprise a slot into which the warmer 20 is inserted and the holder 50 would comprise two heating units 43 to warm both sides of the warmer 20, although the two-sided warmer could still be implemented with the holder 50 as illustrated in FIG. 15.

Third Alternate Embodiment

Figure 21:
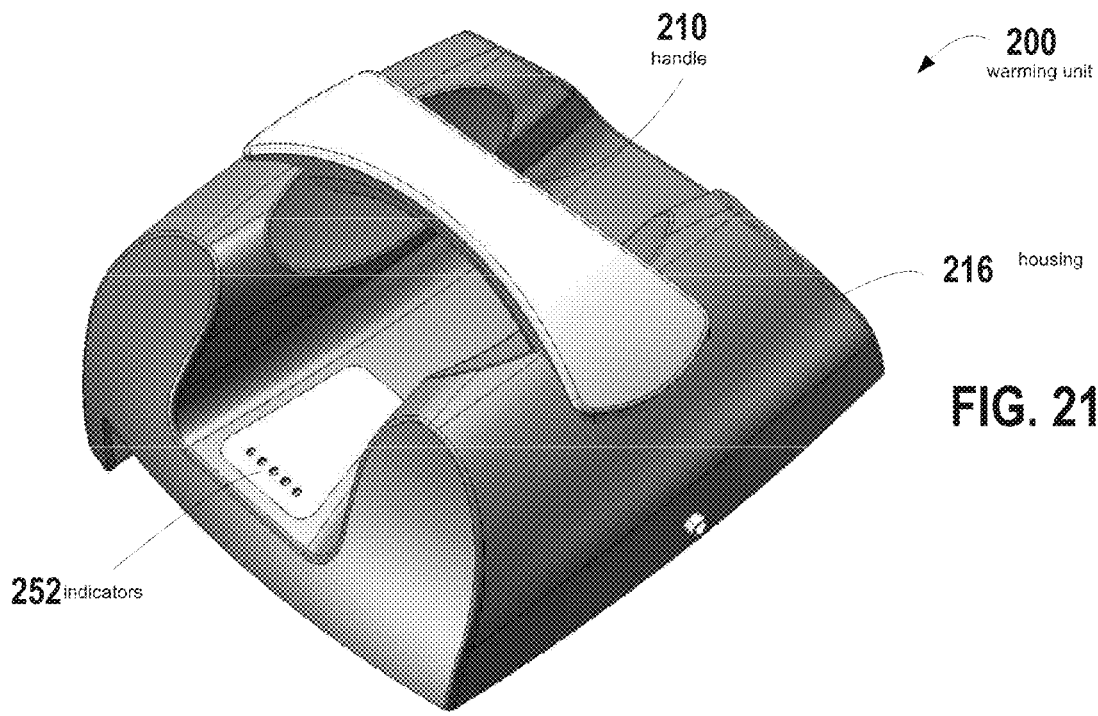
FIG. 21 is a solid front isometric view of a further embodiment of the invention.
Figure 22:
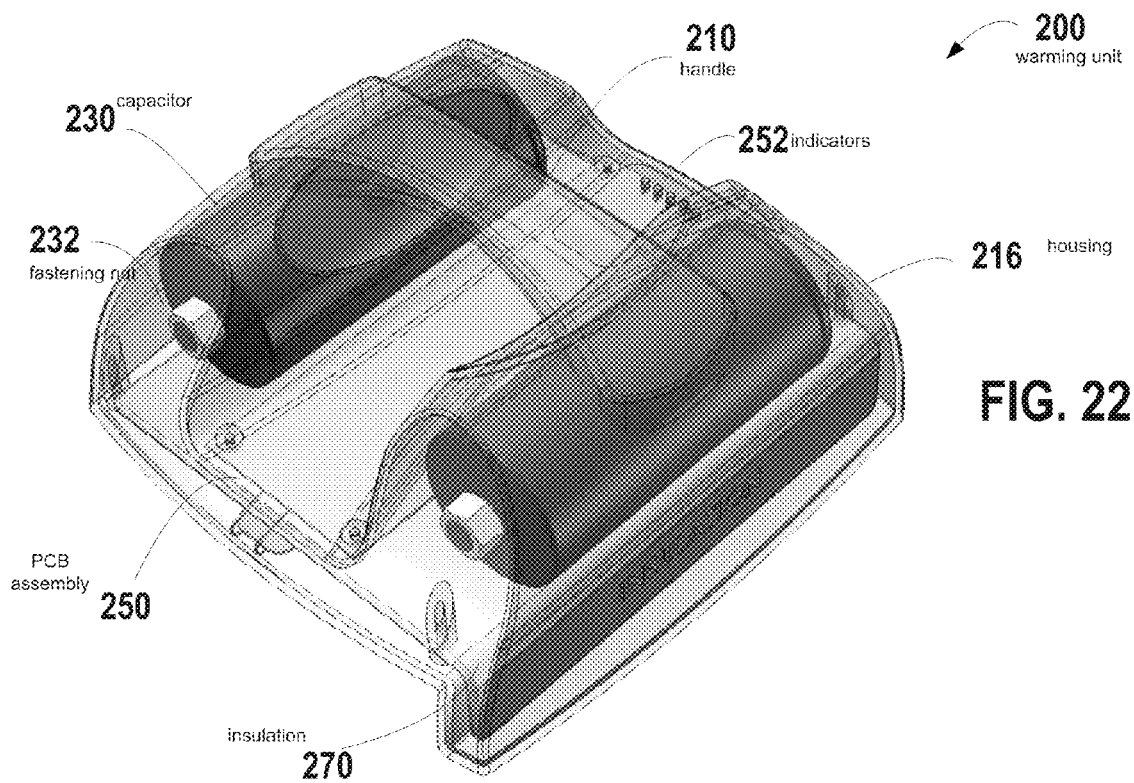
FIG. 22 is a transparent rear isometric view of the embodiment shown in FIG. 21.
Figure 23:
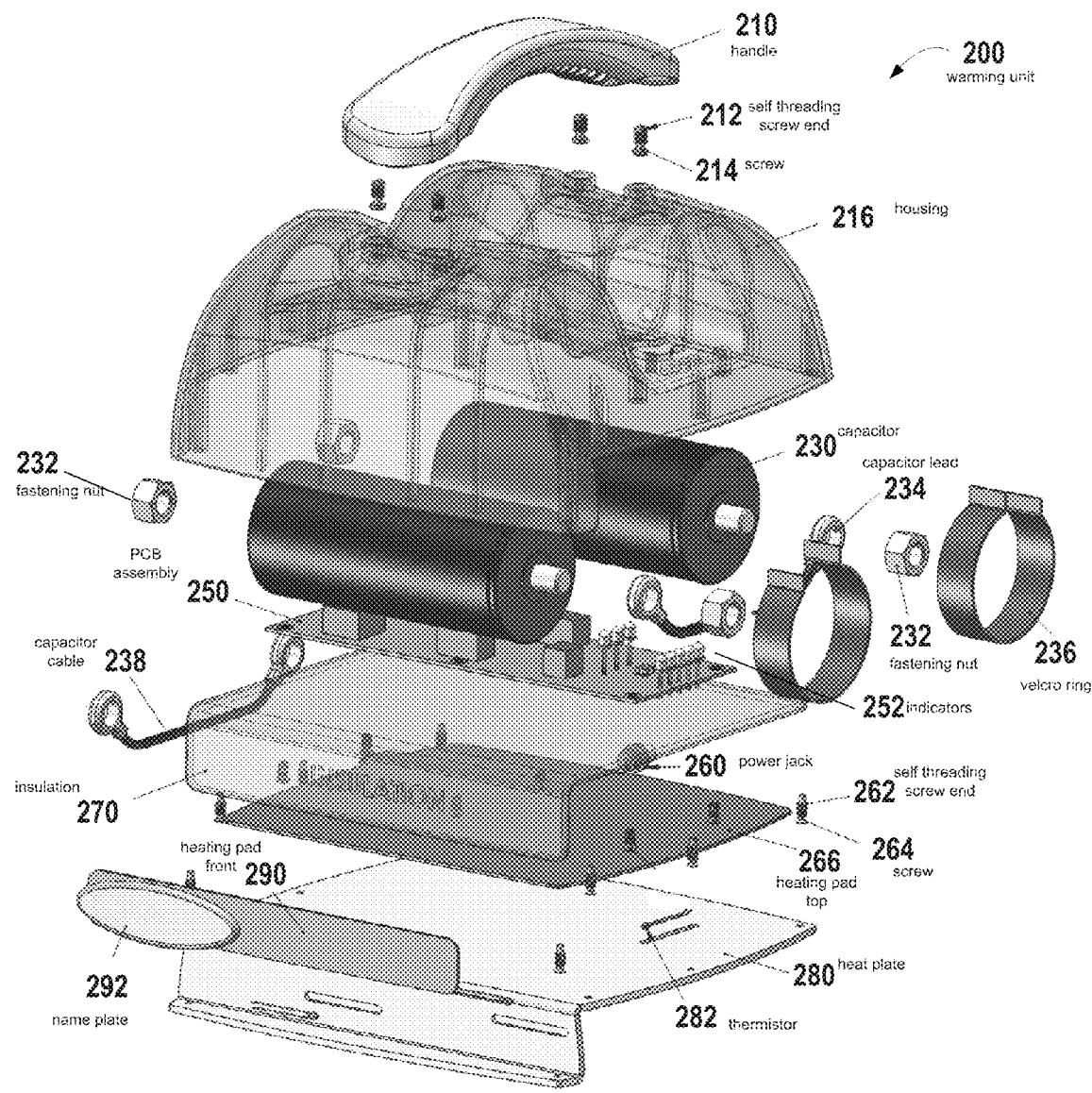
FIG. 23 is an exploded transparent isometric view of the embodiment shown in FIG. 21.

FIGS. 21-23 illustrate a third embodiment of the invention in which the portable warming unit 200 contains the heating element, power supply, and control circuitry, the optional holder (not shown) being used solely to cradle the device and provide access to a power source.

FIG. 21 is an isometric solid view of the portable warming unit 200. In an embodiment of the invention, the housing 216 can be made from a durable material that is lightweight and easy to manufacture, such as a plastic formed by injection molding. The housing could also be formed from metal, preferably a lightweight and inexpensive metal such as aluminum. However, to the extent that the housing is used as part of a thermal mass to hold heat, and that these considerations take precedence over the unit's light weight, it is also possible to use a material having a greater thermal mass to hold the heat. In the preferred embodiment illustrated, the housing comprises smoothed and rounded contours that can generally conform to the contents of the warming unit 200. The housing 216 preferably includes a conductive portion on its body, which is a heat plate (280, 281, FIGS. 22 & 23).

A handle 210 is provided that is firmly affixed to the warming unit 200, and provides a way by which the unit 200 can be easily transported. FIG. 21 also shows a series of indicators 252 that can provide the user with an easy-to-view display of relevant parameters associated with the warming unit 200, such as remaining power or device temperature.

In a preferred embodiment, and as listed in FIG. 21, the unit is preferably a sealed unit, meaning not an open design and one that is generally sealed to contaminants such as dust particles, etc., although additional sealing could be provided around the gaps and holes to further improve the device and make it waterproof. The heating element, power elements, etc. are generally enclosed within the housing 216 and heat plates 280, 281 (FIGS. 21 & 22).

FIG. 22 is an isometric transparent view that illustrates various internal components in addition to those shown in FIG. 21. In FIG. 22, the indicators 252 can be seen with respect to a printed circuit board (PCB) assembly 250 upon which they are mounted. Additionally, the main source of power, the capacitors 230, in this case, can be seen. Furthermore, the location of the top heating pad 266 and front heating pad 290 can be seen, and below these, respectively the top heat plate 280, which contacts the top surface of the bucky, and front heat plate 281, which contacts the front surface of the bucky.

FIG. 23 is an exploded view of the warming unit 200 that shows considerable additional detail. As noted above, the top part of the unit 200 comprises a handle 210 that is used to transport the unit 200. The handle is affixed to the housing 216 that encloses the electronics and can provide a physically attractive contoured surface. For ease of assembly, the handle 210 may be affixed to the housing 216 using screws 214 having self-threading screw ends 212.

In this embodiment, the warming unit 200 comprises its own power storage unit so that the device can continue generating heat after it has been removed from its base. Although any form of power storage could be utilized, such as batteries, it has been found advantageous in a preferred embodiment to utilize large capacitors 230. The capacitors envisioned in a preferred embodiment are the Maxwell Technologies® BCAP3000 Ultracapacitors (specification sheets attached in the concurrently submitted Information Disclosure Statement, herein incorporated by reference). These capacitors are 3000 Farads, operating at 2.7 volts, and advantageously, can operate over one million duty cycles, which is significantly more than known rechargeable batteries, thus providing a significant difference over the maintenance that would be required with the use of rechargeable batteries. Furthermore, there is no charging memory associated with the capacitors as there are for most battery types that would be implemented, and, given the nature of the circuitry, the capacitors are suitable since the circuitry is robust and tolerant of lower voltages—namely, the heaters can simply be left on for a longer period of time when the capacitors are not fully charged.

Given an operating voltage of 2.7 volts, it is preferable that the capacitors be connected in series via a cable 238 affixed with fastening nuts 232 to produce 5.4 volts. In a preferred embodiment, the circuitry is designed to operate with a range of 2.5 to 5.4 volts so that the capacitors 230 can discharge more than halfway before needing to be discharged. In this design, a series of five LED indicators 252 are provided that linearly illustrate the charge within this range. The indicators 252 may further comprise a temperature indication, which, in its simplest form, indicates whether the device is within an acceptable temperature range for operation, and may also provide an indication as to whether the unit is on or off.

A switch 253 may further be provided, that can either disconnect the heating pads 266, 290 from the power source 230, or could disconnect the power source 230 from all else within the warming unit 200. The switch 253 could be covered with a membrane (as could the indicators 252), as illustrated, but not numbered, in FIG. 24A.

Capacitor leads 234 affix connectors to the PCB 250, and the leads are affixed to the capacitors 230 with fastening nuts 234. Ring clamps 235, e.g., Velcro rings, may be provided to help ensure that the capacitors 230 stay in place.

A power jack 260 is provided for recharging the power supply 230. Any appropriate conditioning circuitry, such as rectification or voltage/current level adjustment may be provided.

Power is applied to the top heating pad 266 and the front heating pad 290. In a preferred embodiment, heating pads in the form of those provided by Watlow—Silicone Rubber Heaters are advantageously rugged, thin, lightweight, and flexible. A specification for these heaters is provided in the concurrently filed Information Disclosure Statement, and is herein incorporated by reference. In a preferred embodiment, the top heating pad 266 may have approximate rectangular dimensions of 8"×7.25", and the front heating pad 290 may have approximate rectangular dimensions of 8"×1", although any appropriately sized pad could be used to maximize heat transfer to a bucky.

An insulating layer 270 is provided so that the heat from the heating elements are at least partially isolated from the power supply 230 and circuitry (on PCB 250), and to help contain the heat so that it is maximally conducted through the heat plate 280. The heat plate 280 contacts the surface of the bucky and transfers the heat from the warming unit 200 to the bucky. A front portion may be provided with a plate 292, so that a company logo or other informational indicia may be presented to a user.

The temperature of the element that contacts the bucky must be very precisely controlled, given the dangers of an over-temperature condition, for reasons discussed above. Therefore, in a preferred embodiment, two pairs of thermistors 282 are used, with one pair of thermistors being on the top heat plate 280, and another pair of thermistors being on the front heat plate 281, with each thermistor 282 measuring the temperature of a respective portion of the heating plate 280, 281.

Since it is the temperature of the bucky itself that is important, it is desirable to have the thermistors 282 as close to the bucky as possible in order to get the best temperature reading. Therefore, the heat plates 280, 281 may have slots 283 in which the thermistors 282 reside. The slots are, in a preferred embodiment, may have a thickness of approximately 0.035" or less, i.e., there is 0.035" of the heat plate between the thermistor 282 and the bucky surface. In this way, a very accurate determination of the bucky table temperature can be obtained. Of course, as few as one or as many as is practical thermistors could be used.

Figures 24A, 24B:
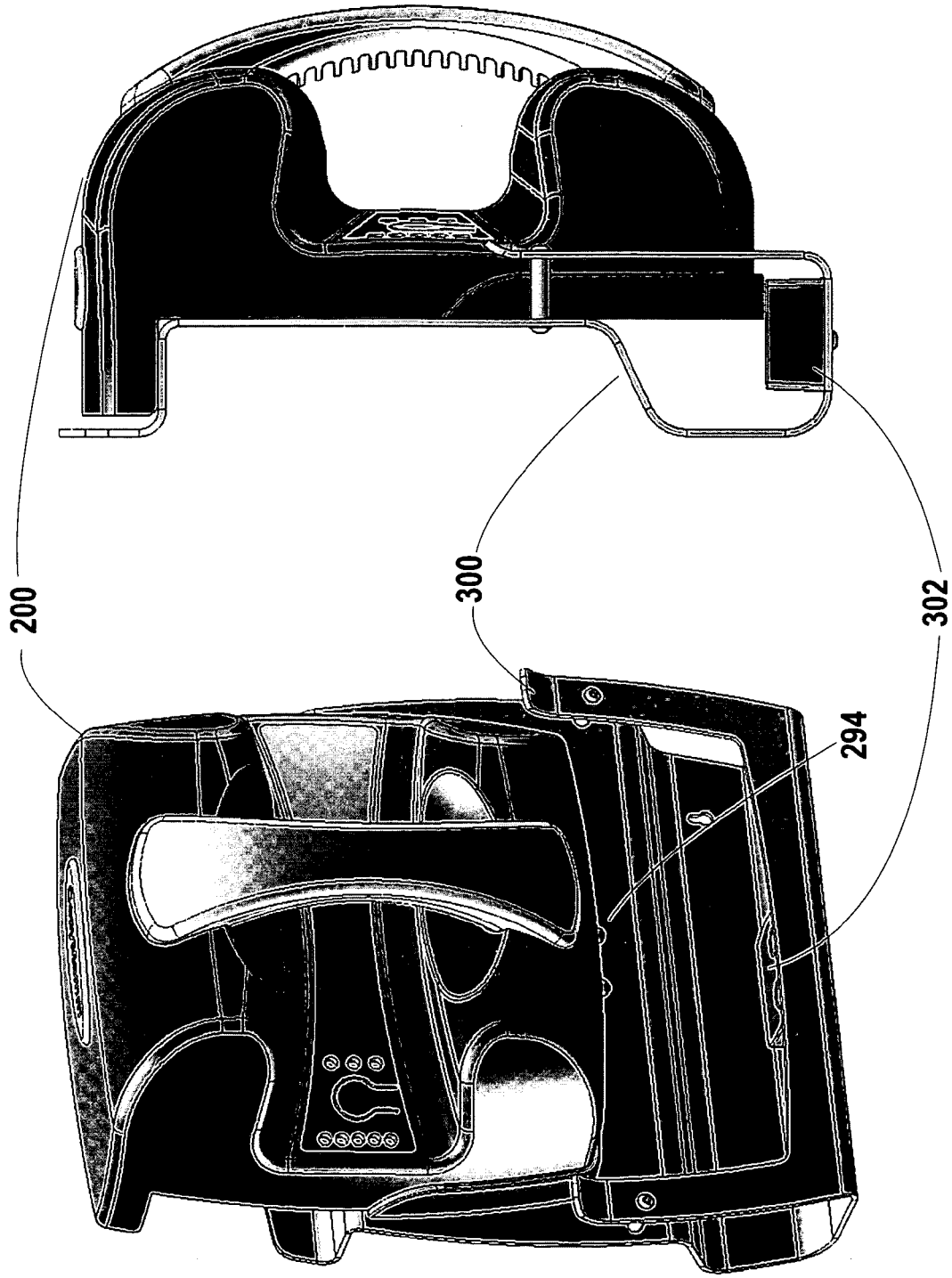
FIG. 24A is an isometric pictorial view of the warming partially inserted into its charging holder.
FIG. 24B is a side pictorial view of the warmer inserted into its charging holder.

FIGS. 24A and B illustrate the warming unit 200 with its charging holder 300. In this variant, the warming unit 200 comprises two charger pins 294 via which the warmer 200 can be charged. The holder 300 comprises a charger plug 302, that may include springs within its holes to received the charger pins 294 and assure a good contact with them when the unit is plugged in for charging. Standard line voltages (110 VAC or 220 VAC (foreign)) can be provided by the holder 300 to the pins 294, in which case rectification and charging conditioning circuitry for charging would be located within the warming unit 200. Alternately, in order to save weight in the warming unit 200, the rectification and charge conditioning circuitry could be located within the holder 300 or other location so that the charger pins 294 receive a proper DC voltage for charging. The approximate charging time for the embodiment using the 3000 F capacitors can range from approximately six to eight minutes. A further advantage to using the capacitors instead of batteries is that they do not degrade over time (or degrade very slowly, compared to batteries), thereby minimizing replacement costs, and, as noted above, do not have a voltage memory and can sustain a significantly larger number of discharge-recharge cycles. Furthermore, the capacitors are much more tolerant to being charged or discharged too fast than are batteries.

Figure 25:
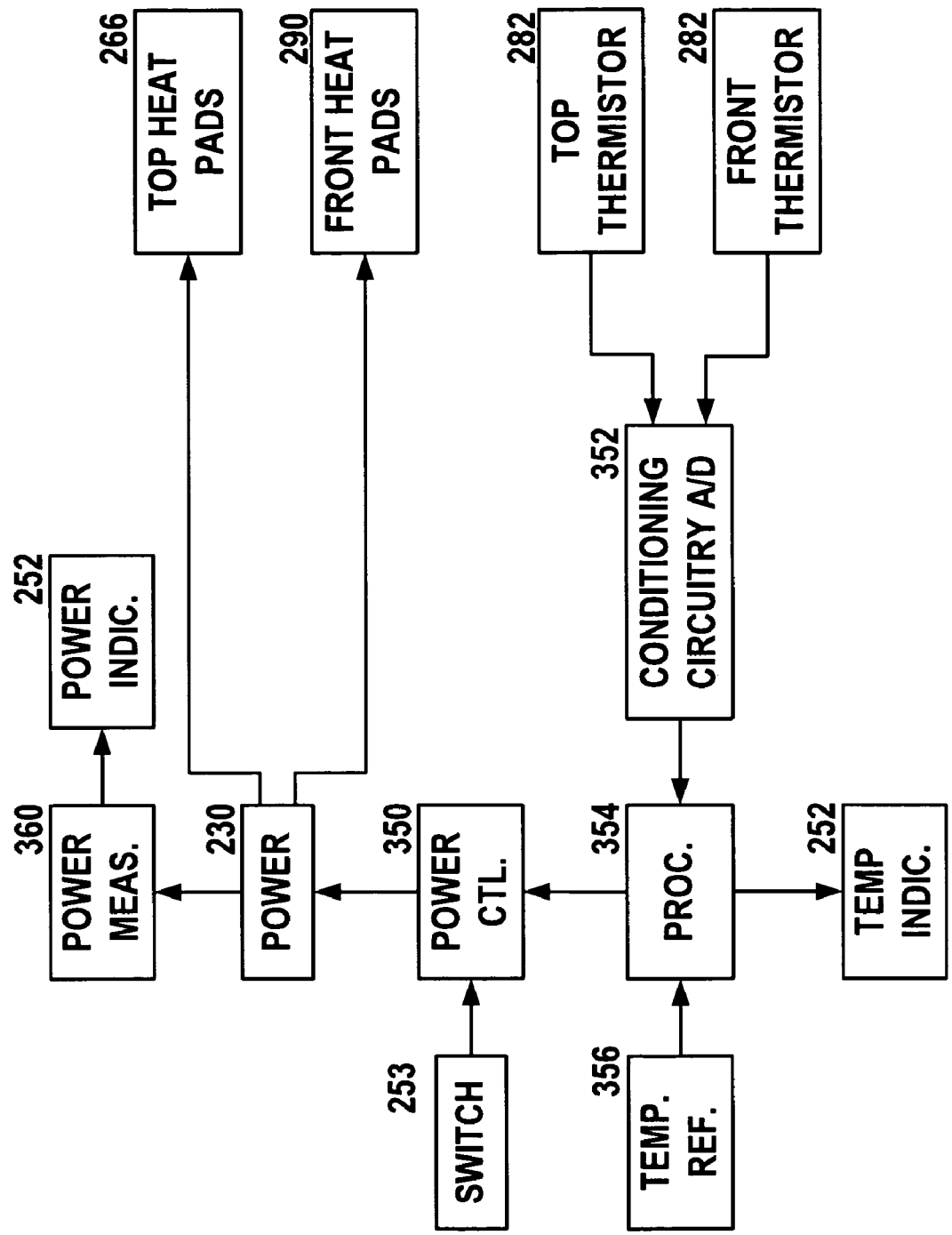
FIG. 25 is a simplified schematic block diagram of the circuitry.

FIG. 25 is a simplified block diagram of the circuitry, some of which may reside on the PCB 250. Referring again to the temperature control, in a preferred embodiment, the pairs of thermistors 282 provide an output that is modified by conditioning circuitry 352 that may include analog-to-digital (A/D) conversion. The processor 354 receives the thermistor output as a temperature or as something easily convertible to temperature. Given the accuracy of the thermistors 282 and associated circuitry 252, the temperature of each thermistor can be determined within approximately a 0.2° F. in the range of usable temperatures.

The processor 354 samples the temperature at each thermistor 282 frequently. In a preferred embodiment, the sample rate is 50 ms or less, although other sampling rates could clearly be used. The information obtained from the thermistors 282 can be used to provide some indication of temperature to the temperature indicator 252. This could be as simple as providing an LED to illuminate when all thermistors are within the desired operating range, or as complex as a temperature reading for an average, min. or max. value of temperature.

More importantly, the processor 354 determines when the proper temperature has been reached and sends an indication to the power control 350 as to whether to connect or disconnect power 230 from the heat pads 266, 290. Various schemes can be envisioned for the control. In a preferred embodiment, if any of the thermistors 282 exceeds a predetermined temperature, then the power to all heating pads 266, 290 is terminated. In another embodiment, the power on a particular heating pad 266, 290 would only be terminated if one of the thermistors 282 associated with that pad indicated a temperature exceeding the predetermined temperature. In addition to the maximum values of temperature being used, the average values could also be used. The processor 354 may perform its recited functions by special algorithms easily developable by one of ordinary skill in the art.

A desired temperature for operation can be set by the temperature reference circuitry 356. This could be provided in a variety of ways, including a simple passive device, such as a potentiometer, that can be read in some manner by the processor, or could be as sophisticated as a value that is entered by a user into a memory associated with the processor 354 and that is subsequently read by the processor 354 for comparison to the measured values.

As noted previously, a switch 253 can also be used to manually provide an input into the power control 350.

FIG. 25 also provides for power measurement circuitry 360 that is used to determine the condition of the power supply 230. The power that is measured can then be transformed in some manner and used to operate the power indicators 252 that can provide an indication of the remaining power available.

Although the invention has been discussed in the context of a mammography machine, the principles of the invention extend beyond such a limited use, and can be applied in any situation where it is desirable to warm the surface of a medical examination apparatus that contacts tissue.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

TABLE OF REFERENCE CHARACTERS 10 bucky warmer system
20 bucky warmer
22 heating element
24 filling material
26 plate
28 covering layer
30 insulating layer
32 bottom surface
34 top surface
35 handle
36 angled end
38 inside surface of angled end
39 contact points
40 control circuitry, processor
42 temperature sensors
43 heating unit
44 user interface portion (e.g., indicator, display, or control panel)
50 holder
52 supporting surface
53 warming surface
54 pins
100 mammography machine
110 bucky
110' paddle
112 top surface of bucky
112' bottom surface of paddle
114 side surface of bucky
114' side surface of paddle
7-1 plastic outside cover
7-2 foam insulation layer
7-3 adhesive backed seal sheet
7-4 heater wire support sheet 7-4
7-5 flocked cloth cover
7-6 heating element
7-7 heating element support tab
7-8 thermal mass
8-1 power input
8-2 power input socket
8-3 wall mount plastic housing
8-4 on/off switch
8-5 positive power lead
8-6 negative spring contact
8-7 positive spring contact
8-8 positive lead terminal
8-9 positive terminal securing rivet
9-1 negative contact disk
9-2 negative printed circuit board contact surface
9-3 temperature indicating LED
9-4 reverse polarity protection diode
9-5 negative heating coil securing screw
9-6 positive heating coil securing screw
9-7 temperature control chip
9-8 thermal fuse
9-9 positive printed circuit board contact surface
9-10 positive contact disk
10-1 insulating block
11-1 flocked cover
11-2 heater wire support
11-3 heating wire
11-4 heater contact and temperature control circuit
11-5 adhesive backed seal sheet
11-6 foam insulation horizontal section
11-7 thermal inertial/mass beads
11-8 vertical section for the foam insulation
11-9 plastic outside cover
12-1 front section plastic housing
12-2 rear cover
12-3 double face tape
13-1 plastic housing
13-2 electric contact terminal
13-3 on/off switch
200 warming unit (third embodiment)
210 handle
212 self-threading screw end
214 screw
216 housing
230 capacitor
232 fastening nut
234 capacitor lead
236 Velcro ring
238 capacitor cable
250 printed circuit board (PCB)
252 indicators
253 switch
260 power jack
262 self-threading screw end
264 screw
266 heading pad top
270 insulation
280 top heat plate
281 front heat plate
282 thermistor
283 thermistor slot
290 heating pad front
292 name plate
294 charger pins
300 holder
302 charger plug
350 power control
352 conditioning circuitry, A/D
354 processor
356 temperature reference
360 power measuring circuitry

What is claimed is:

1. A portable apparatus for warming one or more surfaces of a medical diagnostic or therapeutic instrument, comprising:
   a housing comprising a heat plate that forms a lower surface of the housing, the heat plate designed to contact a surface of the medical diagnostic or therapeutic instrument;
   a handle affixed to the housing;
   wherein the housing contains within:
      a heating element;
      a power supplying element that powers the heating element;
      a power terminal for providing power to the power supplying element;
      a temperature setting mechanism for setting a predefined temperature value; and
      a precision temperature regulator that precisely regulates a temperature of the heat plate to not exceed the predefined temperature value by ±2° F.
   wherein:
      the heat plate comprises:
         a first heat plate part that contacts a first surface of the medical diagnostic or therapeutic instrument; and
         a second heat plate part that is oriented in a substantially different plane than the first heat plate that contacts a second surface of the medical diagnostic or therapeutic instrument; and
      the heating element is comprised of at least two separate heating element units that includes a top heating element unit proximate and oriented parallel to the first heat plate part and a front heating element unit proximate and oriented parallel to the second heat plate part.

2. The apparatus according to claim 1, further comprising:
   a display element for providing an indication to a user of a temperature related to the heating surface of the warmer.

3. The apparatus according to claim 2, wherein the display element is a single LED that indicates the heat plate is at the predefined temperature value.

4. The apparatus according to claim 1, further comprising:
   a display element for providing an indication to a user of an amount of energy present in the power supply element.

5. The apparatus according to claim 4, wherein the display element is a plurality of LEDs.

6. The apparatus according to claim 1, wherein the housing is generally sealed.

7. The apparatus according to claim 6, wherein the housing comprises the heat plate and the heat plate is made of thermally conductive material on its bottom.

8. The apparatus according to claim 1, wherein each of the heating element units is a silicone-rubber pad with embedded heating wires or paths.

9. The apparatus according to claim 1, wherein the power supplying element comprises one or more capacitors.

10. The apparatus according to claim 9, wherein the one or more capacitors have a value of 3000 Farads or greater.

11. The apparatus according to claim 1, further comprising a control to disconnect the power supplying element from the heating element.

12. The apparatus according to claim 1, further comprising a switch to disconnect the power supplying element from the heating element.

13. The apparatus according to claim 1, wherein the precision temperature regulator comprises:
   one or more thermistors, each having an output related to a measured temperature;
   a processor; and
   conditioning circuitry that conditions the output of the one or more thermistors to make the output readable to the processor.

14. The apparatus according to claim 13, wherein the thermistors are located less than or equal to 0.035" from a top surface of the bucky.

15. The apparatus according to claim 13, wherein the thermistors are placed in slots of the heating plate.

16. The apparatus according to claim 13, wherein the processor comprises an algorithm that directs a control to disconnect the power supplying element from the heating element if a predefined criteria is met.

17. The apparatus according to claim 16, wherein the predefined criteria is that one of the one or more thermistors exceeds a predefined value.

18. The apparatus according to claim 16, wherein the one or more thermistors are a plurality of thermistors associated with each heating element unit, and wherein only the heating element unit having a thermistor exceeding a predefined temperature is disconnected from the power supply.

19. The apparatus according to claim 13, wherein the processor samples the output provided by the one or more thermistors every 50 ms or less.

20. The apparatus according to claim 13, wherein the processor disconnects the heating element from the power supplying element if a portion of the heat plate exceeds the predefined temperature by more than 0.2° F.

21. A system comprising:
   the portable apparatus for warming, as claimed in claim 1;
   a holder that holds the portable warming apparatus, the holder further comprising:
      one or more surfaces that generally mate with surfaces of the portable apparatus for holding the portable apparatus in a generally fixed position; and
      a receiving element to receive the power terminal of the portable apparatus for warming and provide power for charging the power supplying element.

22. The system according to claim 21, wherein:
   the power terminal of the portable apparatus comprises two or more pins; and
   the receiving element of the holder comprises two or more holes having springs therein to assist in providing electrical contact between the pins and a power source of the holder.

23. The apparatus according to claim 15, wherein the thermistors are separate from the heating element.

* * * * *